US011717447B2

United States Patent
Brownhill et al.

(10) Patent No.: US 11,717,447 B2
(45) Date of Patent: Aug. 8, 2023

(54) SENSOR ENABLED WOUND MONITORING AND THERAPY APPARATUS

(71) Applicant: Smith & Nephew PLC, Watford (GB)

(72) Inventors: Varuni Rachindra Brownhill, Hull (GB); Nicholas John Collier, Burwell (GB); James Christopher Frake, Foxton (GB); Victoria Jody Hammond, Hull (GB); Edward Yerbury Hartwell, Hull (GB); Allan Kenneth Frazer Grugeon Hunt, Beverley (GB); Gordon John Leather, Leaden Roding (GB); Simon Mark Norman, Cambridge (GB); Charlotte Urwin, Hull (GB)

(73) Assignee: Smith & Nephew PLC, Watford (GB)

( * ) Notice: Subject to any disclaimer, the term of this patent is extended or adjusted under 35 U.S.C. 154(b) by 1041 days.

(21) Appl. No.: 16/301,388

(22) PCT Filed: May 12, 2017

(86) PCT No.: PCT/IB2017/000693
§ 371 (c)(1),
(2) Date: Nov. 13, 2018

(87) PCT Pub. No.: WO2017/195038
PCT Pub. Date: Nov. 16, 2017

(65) Prior Publication Data
US 2019/0290496 A1    Sep. 26, 2019

Related U.S. Application Data

(60) Provisional application No. 62/336,535, filed on May 13, 2016, provisional application No. 62/337,252, (Continued)

(51) Int. Cl.
*A61M 5/00* (2006.01)
*A61F 13/00* (2006.01)
(Continued)

(52) U.S. Cl.
CPC ........ *A61F 13/00059* (2013.01); *A61B 5/445* (2013.01); *A61F 13/00068* (2013.01);
(Continued)

(58) Field of Classification Search
CPC .......... A61M 5/00; A61M 5/32; A61M 25/00; A61M 35/00; A61M 1/00; A61M 5/178;
(Continued)

(56) References Cited

U.S. PATENT DOCUMENTS

| 3,896,802 A | 7/1975 | Williams |
| 4,334,530 A | 6/1982 | Hassell |

(Continued)

FOREIGN PATENT DOCUMENTS

| CN | 105232229 | 1/2016 |
| CN | 105395184 | 3/2016 |

(Continued)

OTHER PUBLICATIONS

International Search Report and Written Opinion, re PCT Application No. PCT/IS2017/000693, dated Jul. 26, 2017.

(Continued)

*Primary Examiner* — Catharine L Anderson
*Assistant Examiner* — Ilya Y Treyger
(74) *Attorney, Agent, or Firm* — Knobbe, Martens Olson & Bear, LLP

(57) ABSTRACT

In some embodiments, a wound dressing that incorporates a number of sensors or sensors separate from the wound dressing can be utilized in order to monitor characteristics of a wound as it heals or to identify one or more risk factors or conditions that may precipitate a wound. In some imple-
(Continued)

mentations, a wound dressing configured to be positioned in contact with a wound includes a substantially flexible substrate supporting one or more sensors. The one or more sensors can include temperature sensors, conductivity sensors, multispectral optical measurements sensors, pH sensors, pressure sensors, colorimetric sensors, optical sensors, ultraviolet (UV) sensors, or infrared (IR) sensors.

32 Claims, 24 Drawing Sheets

Related U.S. Application Data filed on May 16, 2016, provisional application No. 62/484,792, filed on Apr. 12, 2017.

(51) Int. Cl.
| | | |
|---|---|---|
| *A61B 5/00* | (2006.01) | |
| *A61F 13/02* | (2006.01) | |
| *A61M 1/00* | (2006.01) | |
| *A61M 5/32* | (2006.01) | |
| *A61M 25/00* | (2006.01) | |
| *A61M 35/00* | (2006.01) | |
| *A61F 7/00* | (2006.01) | |

(52) U.S. Cl.
CPC .......... *A61F 13/0216* (2013.01); *A61M 1/73* (2021.05); *A61M 1/915* (2021.05); *A61M 1/916* (2021.05); *A61M 1/966* (2021.05); A61F 2013/0097 (2013.01); A61F 2013/00442 (2013.01); A61F 2013/00948 (2013.01); A61F 2013/00953 (2013.01); A61F 2013/00957 (2013.01); A61F 2013/00961 (2013.01); *A61M 1/982* (2021.05); *A61M 1/985* (2021.05); A61M 2205/3306 (2013.01); A61M 2205/3324 (2013.01); A61M 2205/3344 (2013.01); A61M 2205/3368 (2013.01); A61M 2205/3375 (2013.01); A61M 2205/3584 (2013.01); A61M 2230/50 (2013.01); A61M 2230/65 (2013.01)

(58) Field of Classification Search
CPC ...... A61F 13/00; A61F 7/00; A61F 13/00068; A61F 13/00059; A61F 2013/00442; A61F 2013/00948; A61F 2013/00953; A61F 2013/00957; A61F 2013/00961; A61F 2013/0097

See application file for complete search history.

(56) References Cited

U.S. PATENT DOCUMENTS

| | | |
|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 5,904,659 A | 5/1999 | Duarte et al. |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor et al. |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,364,918 B2 | 4/2008 | Prince et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,838,717 B2 | 11/2010 | Haggstrom et al. |
| 7,846,141 B2 | 12/2010 | Weston |
| 7,877,866 B1 | 2/2011 | Greenberg et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,207,392 B2 | 6/2012 | Haggstrom et al. |
| 8,238,996 B2 | 8/2012 | Burnes |
| 8,241,231 B2 | 8/2012 | Bausewein et al. |
| 8,332,053 B1 | 12/2012 | Patterson et al. |
| 8,333,874 B2 | 12/2012 | Currie et al. |
| 8,366,692 B2 | 2/2013 | Weston |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,829,263 B2 | 9/2014 | Haggstrom et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,192,700 B2 | 11/2015 | Weston et al. |
| 9,204,806 B2 | 12/2015 | Stivoric et al. |
| 9,220,455 B2 | 12/2015 | Sarrafzadeh et al. |
| 9,226,402 B2 | 12/2015 | Hsu |
| 9,259,558 B2 | 2/2016 | Tsai |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |

(56) References Cited

U.S. PATENT DOCUMENTS

| | | |
|---|---|---|
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,201,644 B2 | 2/2019 | Haggstrom et al. |
| 10,207,031 B2 | 2/2019 | Toth |
| 10,209,213 B2 | 2/2019 | Kang et al. |
| 10,285,620 B2 | 5/2019 | Jung et al. |
| 10,288,590 B2 | 5/2019 | Hammond et al. |
| 10,321,862 B2 * | 6/2019 | Dalene ............... A61B 5/14553 |
| 10,463,773 B2 | 11/2019 | Haggstrom et al. |
| 10,226,212 B2 | 12/2019 | Duesterhoft et al. |
| 10,857,038 B2 | 12/2020 | Zamierowski et al. |
| 11,026,847 B2 | 6/2021 | Piotrowski et al. |
| 11,229,553 B2 | 1/2022 | Chen et al. |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0132217 A1 | 8/2004 | Prince et al. |
| 2004/0230132 A1 | 11/2004 | Shehada |
| 2005/0088832 A1 | 4/2005 | Su et al. |
| 2005/0228329 A1 | 10/2005 | Boehringer et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0027509 A1 | 1/2008 | Andino et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0092958 A1 | 4/2011 | Jacobs |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0116485 A1 | 5/2012 | Burgmann |
| 2012/0165717 A1 | 6/2012 | Al Khaburi et al. |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0005618 A1 | 1/2014 | Locke et al. |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0066868 A1 | 3/2014 | Freedman et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. et al. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0276454 A1 | 9/2014 | Kuiken et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |

(56) References Cited

U.S. PATENT DOCUMENTS

| | | |
|---|---|---|
| 2016/0074234 A1 | 3/2016 | Abichandi et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0304510 A1 | 10/2017 | Askem et al. |
| 2017/0312456 A1* | 11/2017 | Phillips .................. A61H 23/02 |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribiero et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0001032 A1 | 1/2019 | Weston et al. |
| 2019/0021911 A1 | 1/2019 | Askem et al. |
| 2019/0076298 A1 | 3/2019 | Quintanar et al. |
| 2019/0134280 A1 | 5/2019 | Toth |
| 2019/0159938 A1 | 5/2019 | Askem et al. |
| 2019/0192066 A1 | 6/2019 | Schoess et al. |
| 2019/0231939 A1 | 8/2019 | Askem et al. |
| 2020/0147407 A1 | 5/2020 | Efremkin |
| 2020/0214637 A1 | 9/2020 | Brownhill et al. |

FOREIGN PATENT DOCUMENTS

| | | | |
|---|---|---|---|
| CN | 106102322 | | 11/2016 |
| DE | 10 2012 211015 | | 1/2014 |
| DE | 10 2013 013013 | | 2/2015 |
| EP | 2 454 990 | | 5/2012 |
| EP | 2 565 630 | | 3/2013 |
| EP | 2 574 275 | | 4/2013 |
| EP | 1 734 858 | | 7/2014 |
| EP | 3 231 478 | | 10/2017 |
| EP | 3 409 190 | | 12/2018 |
| EP | 3 499 510 | | 6/2019 |
| GB | 1476894 | | 6/1977 |
| GB | 2316171 | | 2/1998 |
| GB | 2563602 | | 12/2018 |
| JP | 2005052212 A | * | 8/2003 |
| JP | 2009-225863 | | 10/2009 |
| KR | 10 2012 0119523 | | 10/2012 |
| KR | 101224629 B1 | | 1/2013 |
| KR | 10 2014 0024743 | | 3/2014 |
| KR | 10 2014 0058041 | | 5/2014 |
| KR | 10 2016 0071044 | | 6/2016 |
| NL | 1 027 236 | | 4/2006 |
| TW | 200423345 A | * | 10/2002 |
| WO | WO 2000/021433 | | 4/2000 |
| WO | WO 2000/043046 | | 7/2000 |
| WO | WO 2003/067229 | | 8/2003 |
| WO | WO 2006/041997 | | 4/2006 |
| WO | WO 2007/030379 | | 3/2007 |
| WO | WO-2007144795 A1 | | 12/2007 |
| WO | WO 2008/006150 | | 1/2008 |
| WO | WO 2008/010604 | | 1/2008 |
| WO | WO 2010/011920 A2 | * | 7/2008 |
| WO | WO 2009/052607 | | 4/2009 |
| WO | WO 2009/120951 | | 10/2009 |
| WO | WO 2009/141777 | | 11/2009 |
| WO | WO 2010/011920 | | 1/2010 |
| WO | WO 2010/020919 | | 2/2010 |
| WO | WO 2010/105053 | | 9/2010 |
| WO | WO 2011/082420 | | 7/2011 |
| WO | WO 2011/113070 | | 9/2011 |
| WO | WO 2011/123848 | | 10/2011 |
| WO | WO 2012/141999 | | 10/2012 |
| WO | WO 2013/026999 | | 2/2013 |
| WO | WO 2013/044226 | | 3/2013 |
| WO | WO 2013/155193 | | 10/2013 |
| WO | WO 2014/036577 | | 3/2014 |
| WO | WO-2014116816 A1 | | 7/2014 |
| WO | WO 2015/112095 | | 7/2015 |
| WO | WO 2015/168720 | | 11/2015 |
| WO | WO 2016/025438 | | 2/2016 |
| WO | WO 2016/030752 | | 3/2016 |
| WO | WO 2016/058032 | | 4/2016 |
| WO | WO-2016073777 A1 | | 5/2016 |
| WO | WO 2016/100218 | | 6/2016 |
| WO | WO 2016/109744 | | 7/2016 |
| WO | WO 2016/110564 | | 7/2016 |
| WO | WO 2016/187136 | | 11/2016 |
| WO | WO 2016/205872 | | 12/2016 |
| WO | WO 2016/205881 | | 12/2016 |
| WO | WO 2017/021006 | | 2/2017 |
| WO | WO 2017/021965 | | 2/2017 |
| WO | WO 2017/033058 | | 3/2017 |
| WO | WO 2017/037479 | | 3/2017 |
| WO | WO 2017/041014 | | 3/2017 |
| WO | WO 2017/041386 | | 3/2017 |
| WO | WO 2017/041387 | | 3/2017 |
| WO | WO-2017041385 A1 | | 3/2017 |
| WO | WO 2017/119996 | | 7/2017 |
| WO | WO 2017/195038 | | 11/2017 |
| WO | WO 2017/205728 | | 11/2017 |
| WO | WO 2017/214188 | | 12/2017 |
| WO | WO 2018/035612 | | 3/2018 |
| WO | WO 2018/060417 | | 4/2018 |
| WO | WO 2018/064569 | | 4/2018 |
| WO | WO 2018/115461 | | 6/2018 |
| WO | WO 2018/144938 | | 8/2018 |
| WO | WO 2018/144941 | | 8/2018 |
| WO | WO 2018/144943 | | 8/2018 |

(56) References Cited

FOREIGN PATENT DOCUMENTS

| WO | WO 2018/144946 | 8/2018 |
| WO | WO 2018/162728 | 9/2018 |
| WO | WO 2018/162732 | 9/2018 |
| WO | WO 2018/162735 | 9/2018 |
| WO | WO 2018/162736 | 9/2018 |
| WO | WO 2018/185138 | 10/2018 |
| WO | WO 2018/189265 | 10/2018 |
| WO | WO 2018/209090 | 11/2018 |

OTHER PUBLICATIONS

"Little Miss Plasters", kidstravelclub.co.uk., accessed Aug. 26, 2016, in 2 pages. URL: http://www.kidstravelclub.co.uk/little-miss-girls-childrens-plasters.

Aubakir, B. et al., "Vital Sign Monitoring Utilizing Eulerian Video Magnification and Thermography", 2016 38th Annual International Conference of the IEEE Engineering in Medicine and Biology Society, Aug. 16, 2016, pp. 3527-3530, in 4 pages.

Bandodkar, A. et al., "Battery-free, skin-interfaced microfluidic/electronic systems for simultaneous electrochemical, colorimetric, and volumetric analysis of sweat", Science Advances, vol. 5(1), Jan. 18, 2019, in 16 pages. URL: http://advances.sciencemag.org/content/5/1/eaav3294.

Cauwe, M. et al., "Technology development for a low-cost, roll-to-roll chip embedding solution based on PET foils", 18th European Microelectronics and Packaging Conference (EMPC), IEEE, Sep. 12, 2011, in 6 pages.

Farooqui, M. et al., "Low Cost Inkjet Printed Smart Bandage for Wireless Monitoring of Chronic Wounds", Scientific Reports, vol. 6, Jun. 29, 2016, in 14 pages.

Geng, Y. et al., "A Hybrid Low Power Biopatch for Body Surface Potential Measurement", IEEE Journal of Biomedical and Health Informatics, vol. 17(3), May 1, 2013, XP011506375.

Iannetta, R.A. et al., "Successful case histories of polymer based circuitry on flexible film substrates", Electro/94 International Conference Proceedings Combined Volumes, IEEE, May 10-12, 1994, XP010149465.

International Preliminary Report on Patentability, re PCT Application No. PCT/IB2017/000693, dated Nov. 22, 2018.

Jinto, G. et al., "Reliability of Plastic-Encapsulated Electronic Components in Supersaturated Steam Environments", IEEE Transactions on Components, Packaging, and Manufacturing Technology, vol. 5, No. 10, Oct. 2015, in 9 pages.

Lu, B. et al., "A study of the autofluorescence of parylene materials for [mu]TAS applications", Lab on Chip, vol. 10, No. 14, Jul. 2010, pp. 1826-1834, in 9 pages.

McLeod, A. et al., "Motion Magnification for Endoscopic Surgery", Progress in Biomedical Optics and Imaging, SPIE—International Society for Optical Engineering, Mar. 12, 2014, vol. 9036, in 8 pages.

Mostafalu, P. et al., "Wireless Flexible Smart Bandage for Continuous Monitoring of Wound Oxygenation", IEEE Transactions on Biomedical Circuits and Systems, vol. 9, No. 5, Oct. 2015, pp. 670-677, in 8 pages.

Narusawa, H., "The corona discharge causes short destruction that had bad influence on a power switching circuit", Adphox Corporation, Jan. 1, 2009, in 12 pages. URL: http://www.adphox.co.jp/keisokuki/ke-english-corona/CORONA_DISCHARGE_EN.pdf.

Raviglione, A. et al., "Real-Time Smart Textile-Based System to Monitor Pressure Offloading of Diabetic Foot Ulcers", Journal of Diabetes Science and Technology, vol. 11, Sep. 2017, in 5 pages.

Rose, D. et al., "Adhesive RFID Sensor Patch for Monitoring of Sweat Electrolytes", IEEE Transactions on Biomedical Engineering, vol. 62(6), Jun. 2015 (first published Nov. 11, 2015), in 9 pages.

Wakita, J. et al., "Variations in Optical Absorption and Fluorescence Spectra for Polyimide Thin Films Caused by Structural Isomerism", J. Photopolym. Sci. Technol. Jan. 1, 2003, in 1 page.

Willis, B., "Conformal Coating Inspection & Coating Faults", Vision Engineering, Jul. 21, 2016, in 35 pages. URL: http://www.visioneng.com/wp-content/uploads/2017/11/Confirmal-Coating-Inspection-and-Defects.21JUL16.pdf.

Willis, B., "Guide to Conformal Coating & Cleaning Defects Contents", Mar. 1, 2014, in 31 pages. URL: http://coatingguide.smartgroup.org/Files%20pdf/Coating%20Defects%20V2%2014March2014.pdf.

Mehmood N., et al., "Applications of Modern Sensors And Wireless Technology In Effective Wound Management: Modern Sensors And Wireless Technology," Journal of Biomedical Materials Research Part B, vol. 102, May 1, 2014, XP055739544, pp. 885-895.

Grist S.M., et al., "Optical Oxygen Sensors for Applications in Microfluidic Cell Culture," Sensors, 2010, vol. 10 (10), pp. 9286-9316, Retrieved from the Internet: https://doi.org/10.3390/s101009286>https://doi.org/10.3390/s101009286.

* cited by examiner

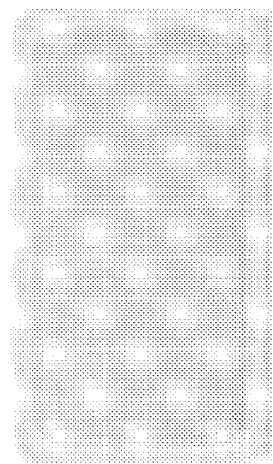
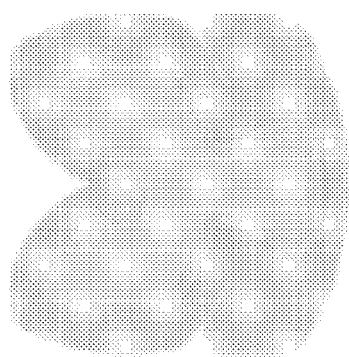
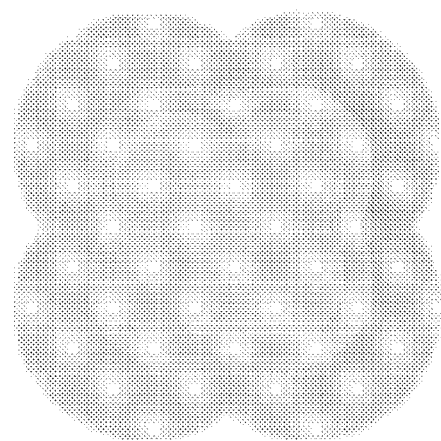
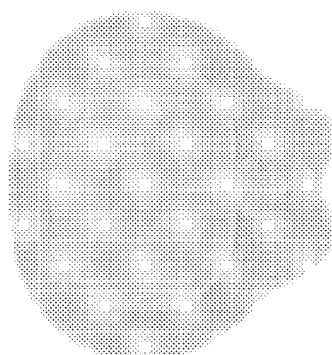
FIG. 2D

SENSOR ENABLED WOUND MONITORING AND THERAPY APPARATUS

CROSS-REFERENCE TO RELATED APPLICATIONS

This application is a U.S. national stage application of International Patent Application No. PCT/IB2017/000693, filed May 12, 2017, which claims priority to U.S. Provisional application Ser. No. 62/484,792, filed Apr. 12, 2017, U.S. Provisional application Ser. No. 62/337,252, filed May 16, 2016, and U.S. Provisional application Ser. No. 62/336,535, filed May 13, 2016, which are hereby incorporated by reference in their entirety.

BACKGROUND

Technical Field

Embodiments described herein relate to apparatuses, systems, and methods for the monitoring or treatment of wounds, for example using dressings in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

However, prior art dressings for use in negative pressure wound therapy or other wound therapy provide little visualization or information of the condition of the wound site beneath the dressing. This can require the dressing to be changed prematurely before the desired level of wound healing has occurred or, for absorbent dressings, prior to the full absorbent capacity of the dressing being reached to allow the clinician to inspect the healing and status of the wound. Some current dressings have limited or unsatisfactory methods or features of providing information of conditions of the wound.

SUMMARY

In some embodiments, a wound monitoring apparatus includes a wound dressing configured to be positioned in contact with a wound and including at least one substantially flexible substrate supporting one or more sensors.

The apparatus of preceding paragraph can include one or more of the following features. The at least one substantially flexible substrate can include a substantially flexible printed circuit, which may include a flexible polymer. The at least one substantially flexible substrate can include a substantially flexible non-conducting mesh. The one or more sensors can include a plurality of sensors electrically connected with each other. The plurality of sensors can be electrically connected with a controller and a power source. The one or more sensors can include one or more temperature sensors, conductivity sensors, multispectral optical measurements sensors, pH sensors, pressure sensors, colorimetric sensors, optical sensors, ultraviolet (UV) sensors, or infrared (IR) sensors.

The apparatus of any of preceding paragraphs can include one or more of the following features. The apparatus can include a controller in electrical communication with the one or more sensors, the control unit configured to receive data from the one or more sensors and communicate the data to a processing device configured to use host software to process the data collected by the one or more sensors to determine one or more conditions associated with the wound. At least one of the controller or the processing device can be configured to indicate, based on the one or more conditions associated with the wound, that the wound is healing. The controller can be configured to wirelessly communicate with at least one of the one or more sensors or the processing device. The controller can be configured to be in electrical communication with at least one of the one or more sensors or the processing device through electrical wiring. The processing device can include a personal computer (PC), a tablet format computing device, a smartphone, or a custom computing device. Data collected by the one or more sensors can be configured to be communicated to the cloud.

The apparatus of any of preceding paragraphs can include one or more of the following features. The wound dressing can include a wound contact layer and the substrate can be positioned on or in the wound contact layer. The wound contact layer can include a first wound contact layer and a second wound contact layer, where the substrate is sandwiched between the first and second wound contact layers. The at least one of the one or more sensors can be configured to be in direct contact with the wound and the at least one of the one or more sensors can be encapsulated between the first wound contact layer and the second wound contact layer. The one or more sensors can include at least a first sensor configured to the in direct contact with the wound and at least a second sensor configured to not contact the wound. The apparatus can include an absorbent layer positioned over the wound contact layer and a backing layer positioned over the wound contact layer, where the wound contact layer is sealed to the backing layer. The apparatus can include a port on the backing layer, the port configured to connect the wound dressing to a source of negative pressure.

The apparatus of any of preceding paragraphs can include one or more of the following features. The wound dressing can be included in a multi-layer wound dressing configured to treat the wound without the use of negative pressure. The apparatus can include a wound packing layer and a drape that are configured to be positioned over the wound separately from the wound dressing. The apparatus can include a negative pressure source configured to be in fluid communication with the wound dressing and further configured to apply negative pressure to the wound.

In some embodiments, a wound monitoring apparatus includes a wound dressing configured to be positioned in contact with one or more of a wound or skin surrounding the wound, the wound dressing including at least one substantially flexible substrate supporting a plurality of sensors. A first sensor of the plurality of sensors can be positioned on the substrate and configured to obtain a measurement of the skin surrounding the wound.

The apparatus of any of preceding paragraphs can include one or more of the following features. A second sensor of the plurality of sensors can be positioned on the substrate and configured to obtain a measurement of the wound. The substrate can be sized to extend at least partially beyond area of the wound and configured to be positioned at least partially over skin surrounding the wound. The wound dressing can include a wound contact layer. The at least one substantially flexible substrate can include at least one of a substantially flexible printed circuit or a substantially flexible non-conducting mesh. The substantially flexible printed circuit can include a flexible polymer. At least some of the plurality of sensors can be electrically connected with each other.

The apparatus of any of preceding paragraphs can include one or more of the following features. The plurality of sensors can be electrically connected with a controller and a power source. The controller can be configured to receive data from the plurality of sensors and communicate the received data to a computing device configured to process the received data to determine one or more conditions associated with the wound. At least one of the controller or the processing device can be configured to indicate, based on the one or more conditions associated with the wound, that the wound is healing The plurality of sensors can include one or more temperature sensors, conductivity sensors, multispectral optical measurements sensors, pH sensors, pressure sensors, colorimetric sensors, optical sensors, ultraviolet (UV) sensors, or infrared (IR) sensors. The plurality of sensors can include a skin elasticity sensor configured to perform an ultrasound sweep of a region of the skin surrounding the wound.

In some implementations, a method of operating or using the apparatus of any of the preceding paragraphs is provided.

In some embodiments, a method of operating a wound monitoring apparatus includes monitoring at least one of a wound or skin surrounding the wound with a wound dressing configured to be positioned in contact with a wound. The wound dressing can include at least one substantially flexible substrate supporting one or more sensors.

The method of the preceding paragraph can include one or more of the following features. The method can include monitoring the skin surrounding the wound with a first sensor positioned on the substrate and monitoring the wound with a second sensor positioned on the substrate. The one or more sensors can include one or more temperature sensors, conductivity sensors, multispectral optical measurements sensors, pH sensors, pressure sensors, colorimetric sensors, optical sensors, ultraviolet (UV) sensors, or infrared (IR) sensors. The substrate can be sized to extend at least partially beyond area of the wound and configured to be positioned at least partially over skin surrounding the wound. The at least one substantially flexible substrate can include at least one of a substantially flexible printed circuit or a substantially flexible non-conducting mesh. The substantially flexible printed circuit can include a flexible polymer. At least some of the one or more sensors can be electrically connected with each other.

The method of the preceding paragraph can include one or more of the following features. The one or more sensors can be electrically connected with a controller and a power source. The method can include, receiving, by the controller, data from the one or more sensors and communicating the received data to a computing device configured to process the received data to determine one or more conditions associated with the wound. The method can include indicating, based on the one or more conditions associated with the wound, that the wound is healing.

BRIEF DESCRIPTION OF THE DRAWINGS

Embodiments of the present disclosure will now be described hereinafter, by way of example only, with reference to the accompanying drawings in which:

FIG. 2D illustrates a wound treatment system employing a wound dressing capable of absorbing and storing wound exudate to be used without negative pressure according to some embodiments;

FIG. 3J shows the intensity loss of light into tissue, and FIG. 3K shows the response of an optical detector;

FIG. 3O illustrates a wound contact layer including holes and curved slits forming a partial circle with slits that extend from the perimeter of the circle to the center of the wound contact layer according to some embodiments;

DETAILED DESCRIPTION

Figure 1A:
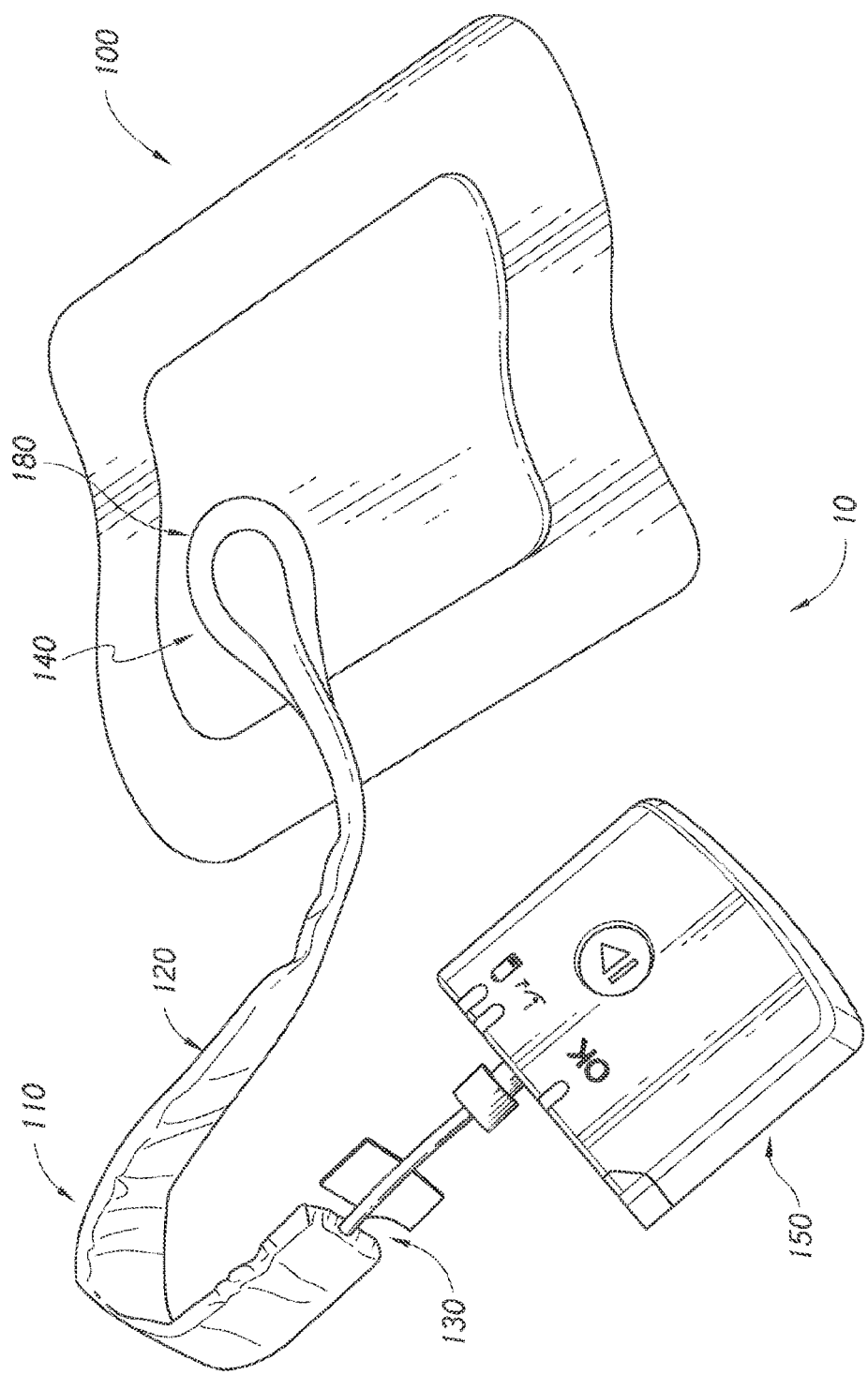
FIG. 1A illustrates a negative pressure wound treatment system employing a flexible fluidic connector and a wound dressing capable of absorbing and storing wound exudate according to some embodiments.

Embodiments disclosed herein relate to apparatuses and methods of monitoring or treating a wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that may benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma, arterial, and venous ulcers or the like.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to monitoring, prevention, and treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). In some embodiments, local ambient atmospheric pressure is used as a reference point, and such local atmospheric pressure may not necessarily be, for example, 760 mmHg. Accordingly, a negative pressure value of −X mmHg reflects absolute pressure that is X mmHg below, for example, 760 mmHg or, in other words, pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg).

The negative pressure range for some embodiments of the present disclosure can be approximately −80 mmHg, or between about −20 mmHg and −200 mmHg or more. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753, 894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS".

NPWT System Overview

Figure 1B:
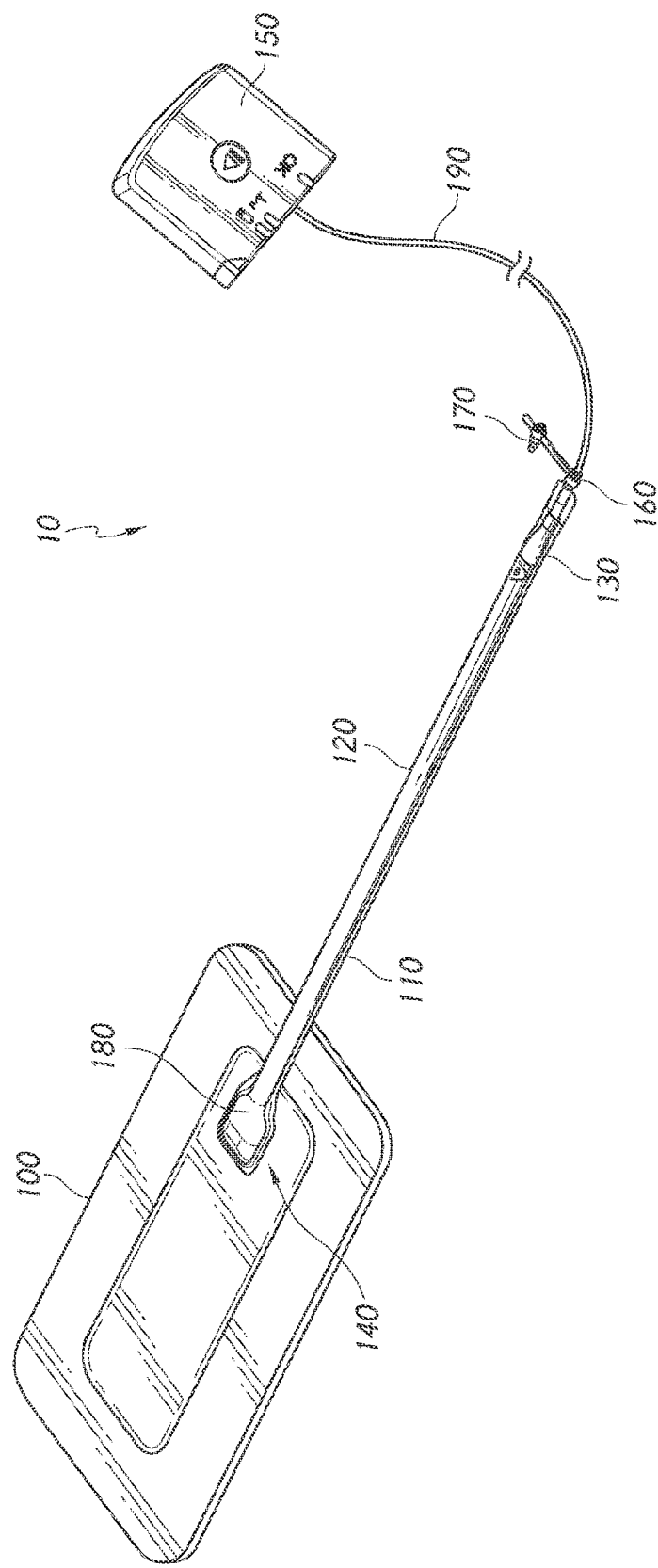
FIG. 1B illustrates a negative pressure wound treatment system employing a flexible fluidic connector and a wound dressing capable of absorbing and storing wound exudate according to some embodiments.

FIGS. 1A-B illustrate embodiments of a negative pressure wound treatment system 10 employing a wound dressing 100 in conjunction with a fluidic connector 110. Here, the fluidic connector 110 may comprise an elongate conduit, such as a bridge 120 having a proximal end 130 and a distal end 140, and an applicator 180 at the distal end 140 of the bridge 120. An optional coupling 160 can be disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Wound Dressing Overview

Figure 2A:
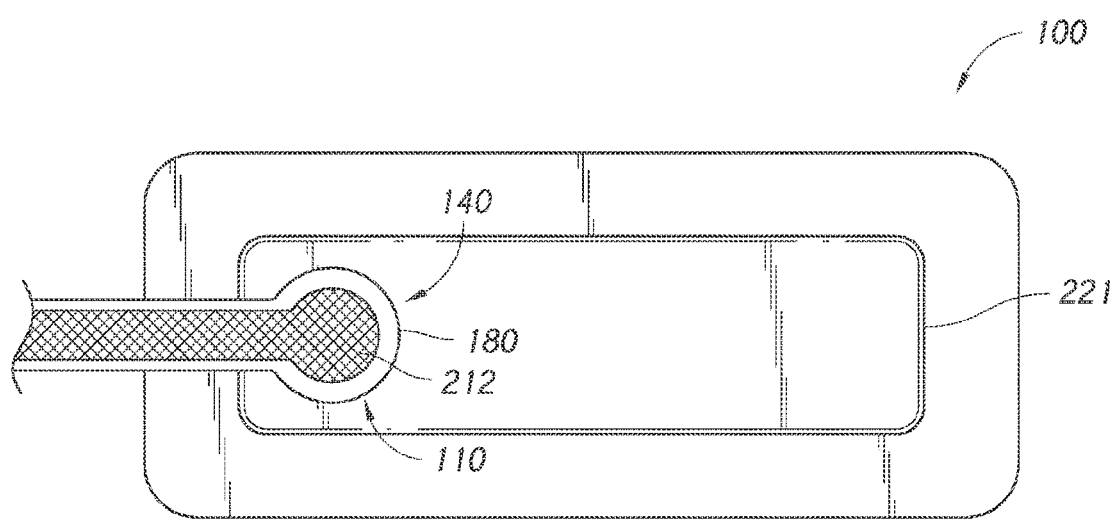
FIG. 2A illustrates a negative pressure wound treatment system employing a flexible fluidic connector and a wound dressing capable of absorbing and storing wound exudate according to some embodiments.

As shown in FIG. 2A, in some embodiments, the fluidic connector 110 can comprise an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In some embodiments, the head 140 may measure 30 mm along its widest edge. The head 140 forms at least in part the applicator 180, described above, that is configured to seal against a top surface of the wound dressing.

Figure 2B:
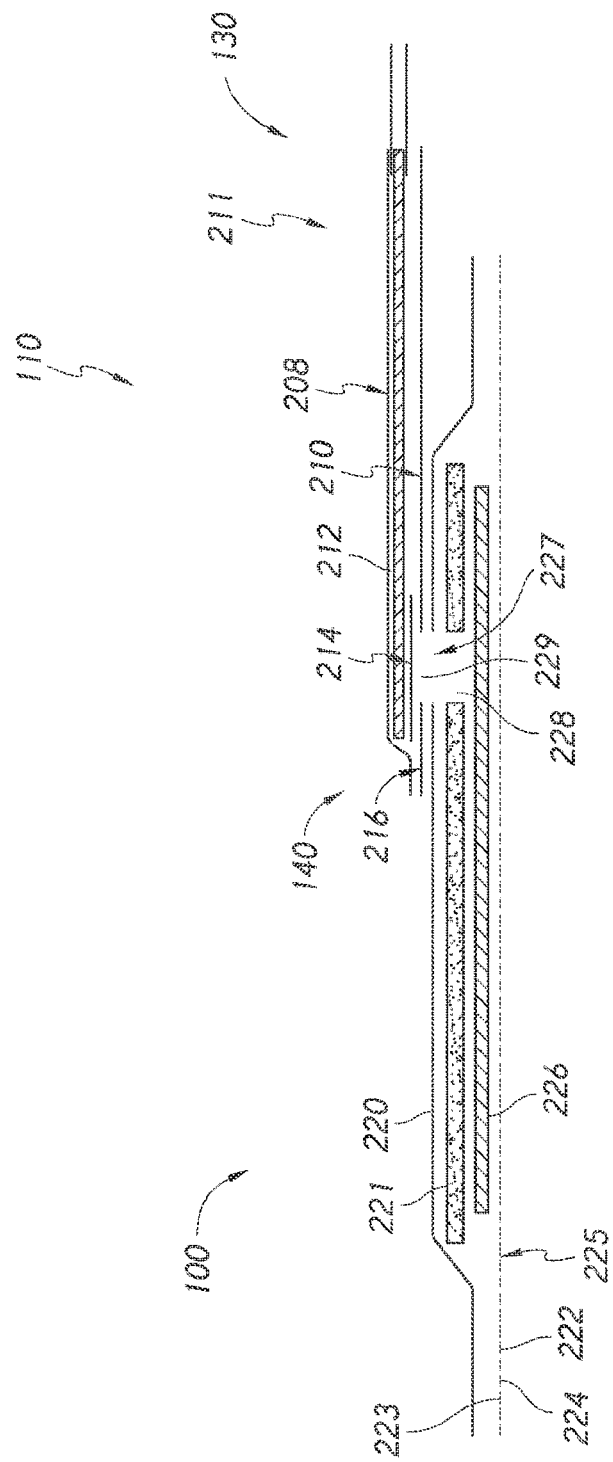
FIG. 2B illustrates a cross section of a fluidic connector connected to a wound dressing according to some embodiments.

FIG. 2B illustrates a cross-section through a wound dressing 100 similar to the wound dressing 10 as shown in FIG. 1B and described in International Patent Publication WO2013175306 A2, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In some embodiments, the dressing 100 comprises a top or cover layer, or backing layer 220 attached to an optional wound contact layer 222, both of which are described in greater detail below. These two layers 220, 222 can be joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 2B, in some embodiments, the wound contact layer 222 can be a polyurethane layer or polyethylene layer or other flexible or substantially flexible layer which is perforated, for example via a hot pin process, laser ablation process, ultrasound process or in some other way or otherwise made permeable to liquid and gas. The wound contact layer 222 has a lower surface 224 (for example, facing the wound) and an upper surface 223 (for example, facing away from the wound). The perforations 225 can comprise through holes in the wound contact layer 222 which enable fluid to flow through the layer 222. The wound contact layer 222 helps prevent tissue ingrowth into the other material of the wound dressing. In some embodiments, the perforations are small enough to meet this requirement while still allowing fluid to flow therethrough. For example, perforations formed as slits or holes having a size ranging from 0.025 mm to 1.4 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 can ensure that an open air channel can be maintained to communicate negative pressure over the wound area even when the absorbent layer has absorbed substantial amounts of exudates. In some embodiments, the layer 226 should remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

In some embodiments, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and can act so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or Chem-Posite™11C-450. In some embodiments, the absorbent layer 221 may comprise a composite comprising superabsorbent powder, fibrous material such as cellulose, and bonding fibers. In some embodiments, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

In some embodiments, an aperture, hole, or orifice 227 is provided in the backing layer 220 to allow a negative pressure to be applied to the dressing 100. In certain implementations, the fluidic connector 110 is attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

In some embodiments, the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 can be provided in the absorbent layer 221 beneath the orifice 227 such that the orifice is connected directly to the transmission layer 226 as illustrated in FIG. 2B. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

In some embodiments, the backing layer 220 is gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 can be sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 can comprise two layers; a polyurethane film and an adhesive pattern spread onto the film. The polyurethane film can be moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

For example, in embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Turning now to the fluidic connector 110, some embodiments comprise a sealing surface 216, a bridge 211 (corresponding to bridge 120 in FIGS. 1A-1B) with a proximal end 130 and a distal end 140, and a filter 214. The sealing surface 216 can form the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 100 similar to the suction adapter as described in U.S. Pat. No. 8,801,685, which is incorporated by reference herein in its entirety.

In some embodiments, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are can be suited to channeling wound exudate away from the wound and for transmitting negative pressure or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; such as, the wicking fabric may be between 3 mm and 6 mm thick, and may be comprised of either one or several individual layers of wicking fabric. In other embodiments, the fluid passage 212 may be between 1.2-3 mm thick, such as thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system can be conformable and soft, which may help to avoid pressure ulcers and other complications which may result from a wound treatment system being pressed against the skin of a patient.

In some embodiments, the filter element 214 is impermeable to liquids, but permeable to gases, and is provided to act as a liquid barrier and to ensure that no liquids are able to escape from the wound dressing 100. The filter element 214 may also function as a bacterial barrier. Typically the pore size is 0.2 µm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments, filter element 214 comprises a support layer and an acrylic co-polymer membrane formed on the support layer. In some embodiments, the wound dressing 100 uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Figure 2C:
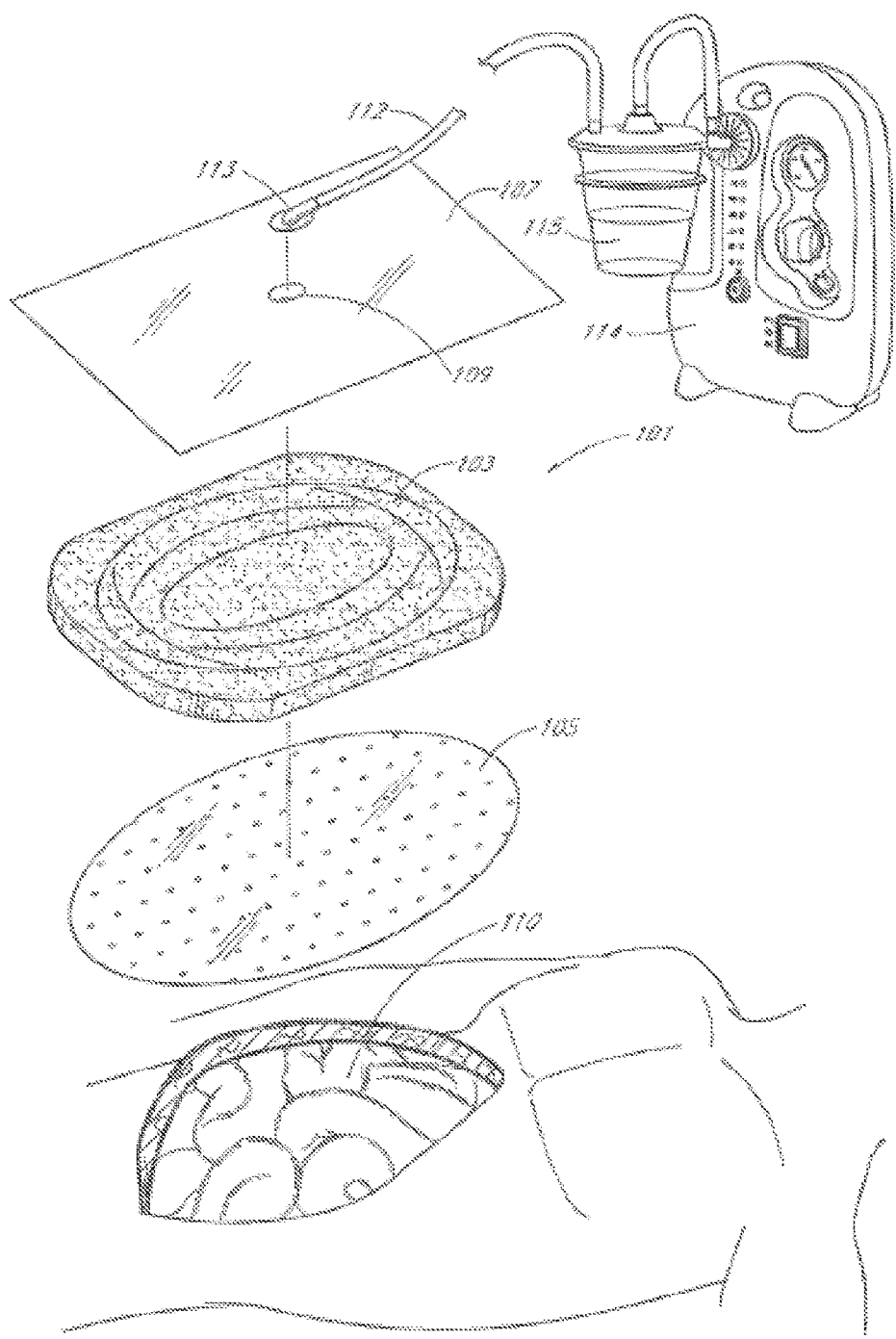
FIG. 2C illustrates a negative pressure wound therapy system according to some embodiments.

Turning to FIG. 2C, in some embodiments, treatment of other wound types, such as larger abdominal wounds, with negative pressure in certain embodiments uses a negative pressure treatment system 101 as illustrated schematically here. In some embodiments, a wound site 106, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, such as using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 106 can be beneficial to a patient.

Accordingly, certain embodiments provide for a wound contact layer 105 to be placed over the wound site 106. The wound contact layer can also be referred to as an organ protection layer or a tissue protection layer. In some embodiments, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 106 or the transmittal of negative pressure to the wound site 106. Additional embodiments of the wound contact layer 105 are described in further detail below.

Certain embodiments of the negative pressure treatment system 101 may also use a porous wound filler 103, which can be disposed over the wound contact layer 105. This pad 103 can be constructed from a porous material, for example foam, that is soft, resiliently flexible, and generally conformable to the wound site 106. Such a foam can include an open-celled and reticulated foam made, for example, of a polymer. Suitable foams include foams composed of, for example, polyurethane, silicone, and polyvinyl alcohol. In some embodiments, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, or length can have other suitable values. Other embodiments of wound fillers that may be used in place of or in addition to the pad 103 are discussed in further detail below.

In certain implementations, a drape 107 is used to seal the wound site 106. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic or oleophobic filter in the container to prevent overflow; other embodiments may include sensing means, such as capacitive sensors or other fluid level detectors that act to stop or shut off the source of negative pressure should the level of fluid in the container be nearing capacity. In some embodiments, at the pump exhaust an odor filter, such as an activated charcoal canister, is provided.

FIG. 2D illustrates various embodiments of a wound dressing that can be used for healing a wound without negative pressure. As shown in the dressings of FIG. 2D, the wound dressings can have multiple layers similar to the dressings described with reference to FIGS. 1A-1B and 2A-2B except the dressings of FIG. 2D do not include a port or fluidic connector. The wound dressings of FIG. 2D can include a cover layer and wound contact layer as described herein. The wound dressing can include various layers positioned between the wound contact layer and cover layer. For example, the dressing can include one or more absorbent layers or one or more transmission layers as described herein with reference to FIGS. 1A-1B and 2A-2B. Additionally, some embodiments related to wound treatment comprising a wound dressing described herein may also be used in combination or in addition to those described in U.S. Application Publication No. 2014/0249495, filed May 21, 2014, entitled "WOUND DRESSING AND METHOD OF TREATMENT" the disclosure of which are hereby incorporated by reference in its entirety, including further details relating to embodiments of wound dressings, the wound dressing components and principles, and the materials used for the wound dressings.

Sensor Enabled Dressings

A wound dressing that incorporates a number of sensors or sensors separate from the wound dressing can be utilized in order to monitor characteristics of a wound as it heals or to identify one or more risk factors or conditions that may precipitate a wound. Collecting data from the wounds that heal well, and from those that do not, can provide useful insights towards identifying measurements or measurands to indicate one or more conditions, including whether a wound is on a healing trajectory, whether the dressing needs to be adjusted, whether therapy parameters needs to be adjusted, or the like. This can enable one or more adjustments to be made. For example, operating parameters of a negative pressure wound therapy device (such as, pressure level, therapy intensity, therapy duration, etc.) can be adjusted. One or more sensors can be used to measure various physiological parameters as described herein.

Figure 3A:
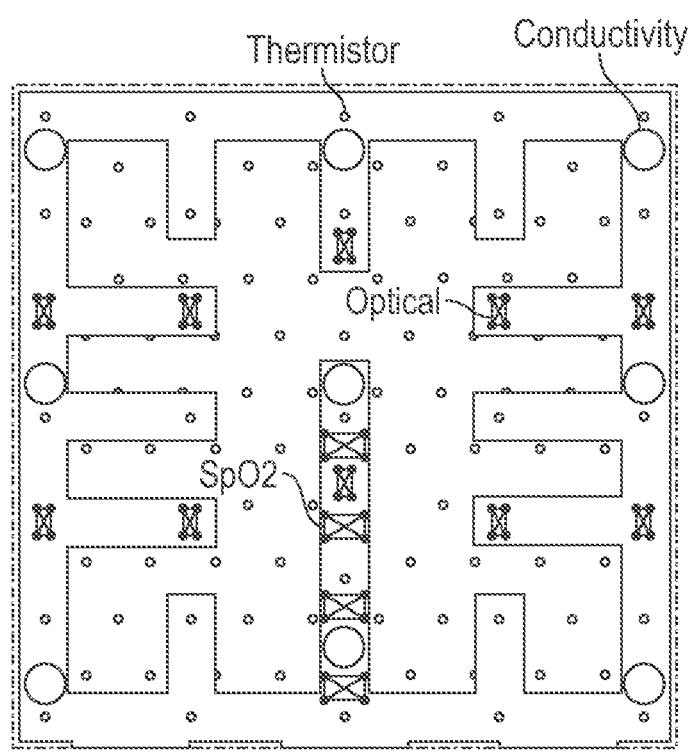
FIG. 3A illustrates a sensor array illustrating the sensor placement incorporated into a wound dressing component according to some embodiments.
Figure 3B:
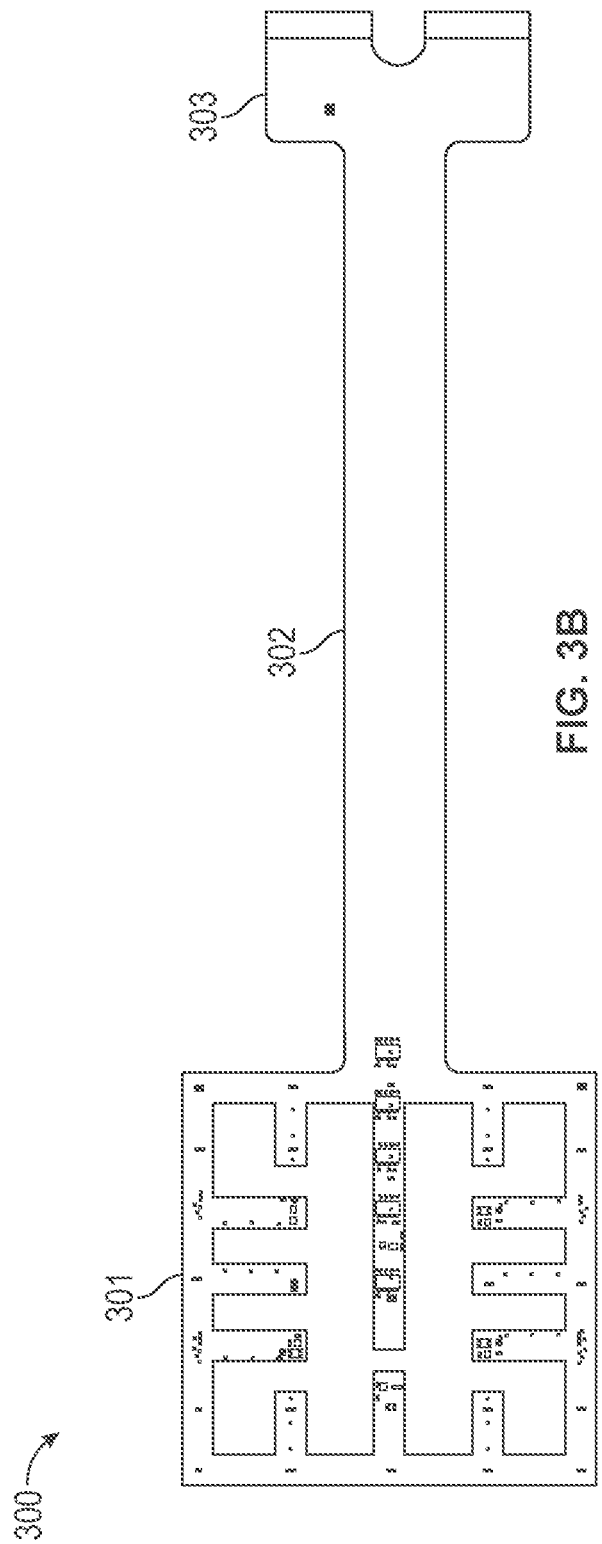
FIG. 3B illustrates a flexible sensor array including a sensor array portion, a tail portion, and an connector pad end portion according to some embodiments.
Figure 3F:
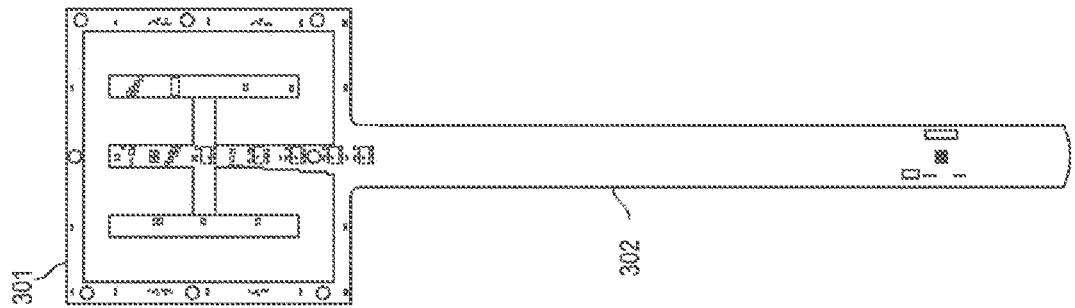
FIGS. 3C-3F show embodiments of the flexible printed circuits with four different sensor array geometries.
Figure 3E:
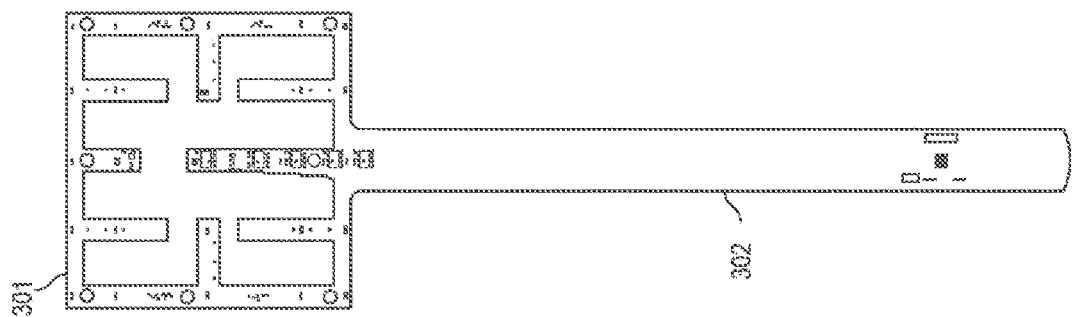

A number of sensor technologies can be used in wound dressings or one or more components forming part of an overall wound dressing apparatus. For example, as illustrated in FIGS. 3A and 3H, in some embodiments, sub-sets of sensors can be incorporated onto or into a wound contact layer, which may be a perforated wound contact layer as shown in FIG. 3H. The wound contact layer in FIGS. 3A and 3H is illustrated as having a square shape, but it will be appreciated that the wound contact layer may have other shapes such as rectangular, circular, oval, etc. In some embodiments, the sensor integrated wound contact layer can be provided as an individual material layer that is placed over the wound area and then covered by a wound dressing apparatus or components of a wound dressing apparatus similar to those described with reference to FIG. 2C (such as, gauze, foam or other wound packing material, a superabsorbent layer, a drape, a fully integrated dressing like the Pico or Allevyn Life dressing, etc.). In other embodiments, the sensor integrated wound contact layer may be part of a single unit dressing such as described in FIGS. 1A-2B and 2D.

The sensor integrated wound contact layer can be placed in contact with the wound and will allow fluid to pass through the contact layer while causing little to no damage to the tissue in the wound. The sensor integrated wound contact layer can be made of a flexible material such as silicone and can incorporate antimicrobials or other therapeutic agents known in the art. In some embodiments, the sensor integrated wound contact layer can incorporate adhesives that adhere to wet or dry tissue. In some embodiments, the one or more sensors, a sensor package, or a sensor array can be incorporated into or encapsulated within other components of the wound dressing such as the absorbent layer or spacer layer described above.

As shown in FIGS. 3A and 3H, a sub-set of five sensors can be used including sensors for temperature (such as, 25 thermistor sensors, in a 5×5 array, ~20 mm pitch), pulse oximetry or SpO2 (such as, 4 or 5 SpO2 sensors, in a single line from the center of the wound contact layer to the edge thereof, 10 mm pitch), optical properties of the tissue, exudate, or foreign bodies (such as, 10 optical sensors, in 2×5 array, ~20 mm pitch; not all 5 sensors in each row of the array need be aligned), pH (such as, by measuring colour of a pH sensitive pad, optionally using the same optical sensors as for tissue colour), and conductivity (such as, 9 conductivity contacts, in a 3×3 array, ~40 mm pitch). In some embodiments, SpO2 is an estimate of arterial oxygen saturation. As shown in FIG. 3A, in some embodiments, the SpO2 sensors can be arranged in a single line from the center of or near the center of the wound contact layer to the edge of the wound contact layer. The line of SpO2 sensors can allow the sensors to take measurements in the middle of the wound, at the edge or the wound, or on intact skin to measure changes between the various regions. In some embodiments, the wound contact layer or sensor array can be larger than the size of the wound to cover the entire surface area of the wound as well as the surrounding intact skin. The larger size of the wound contact layer or sensor array and the multiple sensors can provide more information about the wound area than if the sensor was only placed in the center of the wound or in only one area at a time. Other sensors, such as pressure, flow, strain, colorimetric sensors configured to measure biological or chemical compounds (for example, dye coated colorimetric sensors) or the like, can be additionally or alternatively used. Colorimetric sensors can be used for measure odor, toxicity, etc. Any one or more sensors described herein can be placed or positioned to obtain measurements of any location in the wound or the skin.

The sensors can be supported by or incorporated onto a flexible or substantially flexible substrate, such as one or more of flexible or substantially flexible printed circuits (FPCs) which can be formed from flexible polymers including polyamide, polyimide (PI), polyester, polyethylene naphthalate (PEN), polyetherimide (PEI), polyurethane, thermoplastic polyurethane (TPU), along with various fluropolymers (FEP) and copolymers, or any other suitable material. Although the description can refer to one or more substantially flexible or flexible printed circuits, which may include circuit boards, other types of flexible or substantially flexible substrates, such as one or more non-conductive materials or meshes or woven fabric conductive fibers, can be alternatively or additionally used. For example, one or more of wound dressing components, such as the wound contact layer, can include conductive or non-conductive material(s). Substantially flexible or flexible substrates can include single-sided, double-sided, or multi-layer circuits. In some implementations, the sensor array can be incorporated into a two-layer flexible circuit. In some embodiments, the FPC can be a multi-layer flexible printed circuit. In some embodiments, these flexible printed circuits can be incorporated into any layer of the wound dressing. In some embodiments, a flexible circuit can be incorporated into (for example, positioned on or in) a wound contact layer. For example, the flexible circuit can be incorporated into a wound contact layer similar to the wound contact layer described with reference to FIGS. 2B and 2C. The wound contact layer can have cutouts or slits that allow for one or more sensors to protrude out of the lower surface of the wound contact layer and contact the wound area directly.

In some embodiments, the sensor integrated wound contact layer can include a first and second wound contact layer with an FPC sandwiched between the two layers of wound contact layer material. The first wound contact layer has a lower surface intended to be in contact with the wound and an upper surface intended to be in contact with the FPC. The second wound contact layer has a lower surface intended to be in contact with the FPC and an upper surface intended to be in contact with a wound dressings or one or more components forming part of an overall wound dressing apparatus. The upper surface of the first wound contact layer and the lower surface of the second wound contact layer can be adhered together with the FPC sandwiched between the two layers.

In some embodiments, the one or more sensors of the FPC can be fully encapsulated or covered by the wound contact layers to prevent contact with moisture or fluid in the wound. In some embodiments, the first wound contact layer can have cutouts or slits that allow for one or more sensors to protrude out of the lower surface and contact the wound area directly. For example, the one or more SpO2 sensors as shown in FIG. 3H are shown protruding out the bottom surface of the wound contact layer. In some embodiments, the SpO2 sensors or other sensors can be mounted directly on a lower surface of the first wound contact layer so as to be in direct contact with the wound. Some or all of the sensors and electrical or electronic components may be potted to not be in direct contact with the wound or encapsulated (for example, rendered substantially waterproof or liquid-proof and biocompatible) with a suitable material, such as polymer and for example, silicon or epoxy based polymers. The encapsulation with a polymer can prevent ingress of fluid and leaching of chemicals from the components. In some embodiments, the wound contact layer material can seal the components from water ingress and leaching of chemicals. One or more sensors and electrical or electronic components can be completely potted or embedded and configured to communicate wirelessly to prevent contact with liquids.

In some implementations, one or more sensors can be arranged or deployed in alternative or additional ways as follows. Sensors can be arranged as a strip or string. Sensors can be laid into or in a scaffold, which may be inductively powered. The scaffold may also communicate with a control module or another processing device as described herein. Sensors can be positioned or cast into the foam of the wound dressing or into another matrix configured to fill the wound. Sensors can be mounted onto foam (or other matrix) projections or protrusions that fit into the wound. For example, sensors can be mounted onto protrusions in superabsorbent foam or another superabsorbent material and may extend into the wound upon exposure to wound exudate. Sensors can be incorporated into a deployment material or system separate from the wound dressing. Sensors can be encapsulated into or mounted onto a wound packing material or under-layer, which can be made of Durafiber or duraTouch. For example, sensors can be stitched into gauze or Durafiber dressing made by Smith & Nephew. A customized three-dimensional mold can be cut out or constructed for a particular wound autonomy or geometry in order to correctly position the sensors. Sensor array, arrangement, or package can be rotationally symmetric or substantially rotationally symmetric so that it is less prone to being impacted by rotational misalignment. Sensors can be coated with hydrophobic or hydrophilic substance to prevent exudate coating or depositing on the sensors and adversely affecting measurements. For example, optical sensors can be coated with hydrophobic substance to repel liquid for performing measurements. As another example, pH sensors can be coated with hydrophilic substance to absorb exudate for performing measurements. Sensors can include one or more irrigating channels or flow paths to flush the sensors. For example, this can be used to remove exudate or material from one or more regions of interest to improve measurement accuracy. One or more flow paths can additionally or alternatively be used to channel exudate to a specific location (such as, a sensor or group of sensors) to improve measurement accuracy. This can, for example, generate a larger signal-to-noise ratio or separate a particular sensor or group of sensors from a vulnerable area of the wound).

In certain embodiments, sensor array, arrangement, or package can include one or more alignment marks, edges, or features that can be aligned or co-registered with one or more marks, edges, stickers, or anatomical features to ensure correct placement. For example, alignment of the sensors with the wound or skin or tissue surrounding the wound can be improved. In some cases, sensor array, arrangement, or package can register itself with electromagnetic tags placed on or near the wound, which can assist with positioning and rotating the sensors correctly with respect to the tags and the wound. Images of the sensor array, arrangement, or package after its placement can be taken to analyze the orientation of the sensors. This information can be used to assess positioning of the sensors or to facilitate proper positioning when the sensors are replaced (for example, when dressing is discarded). One or more string or strip sensors can be used to limit orientation errors. An alignment ring can be removably or semi-permanently attached or printed around the wound to allow for accurate positioning when wound dressing is replaced. In case when sensor array, arrangement, or package is deformable or substantially deformable, individual sensors can be configured to register their position with respect to other sensors to analyze positioning or alignment.

One or more pressure monitors (such as one or more strain gauges) can be included to monitor if the wound dressing is too tight or too loose. Feedback from one or more pressure monitors can be used to indicate if the dressing needs to be tightened or loosened. This can be advantageously utilized with compression bandaging.

In some embodiments, gathering and processing information related to the wound can utilize three components, including a sensor array, a control module, and processing software. These components are described in more detail herein.

As described above, the sensor array of FIG. 3A can include a temperature sensor, conductivity sensor, optical sensor, and SpO2 sensor. The flexible sensor array printed circuit 300 includes a sensor array portion 301, a tail portion 302, and an connector pad end portion 303 as shown in FIG. 3B. The sensor array portion 301 can include the sensors and associated circuitry. The sensor array printed circuit 300 can include a long tail portion 302 extending from the sensor array portion 301. The connector pad end portion 303 can be enabled to electrically or electronically connect to a control module or other processing unit to receive the data from the sensor array circuit. The long tail portion 302 can allow the control module to be placed distant from the wound and in a more convenient location. An overall view of one of the sensor arrays printed circuit 300 is shown in FIG. 3B.

In certain implementations, a controller (such as, a microprocessor) can be mounted on the dressing and connected to the sensors. Such mounted controller can communicate with a control module over a simple connection, such as 3 or 4 wire connection (or less or more wires), to alleviate burdens associated with connecting to external component(s). For example, the long tail portion 302 can include a 3 or 4 wire connection. In some implementations, the mounted controller can communicate wirelessly.

Figure 3D:
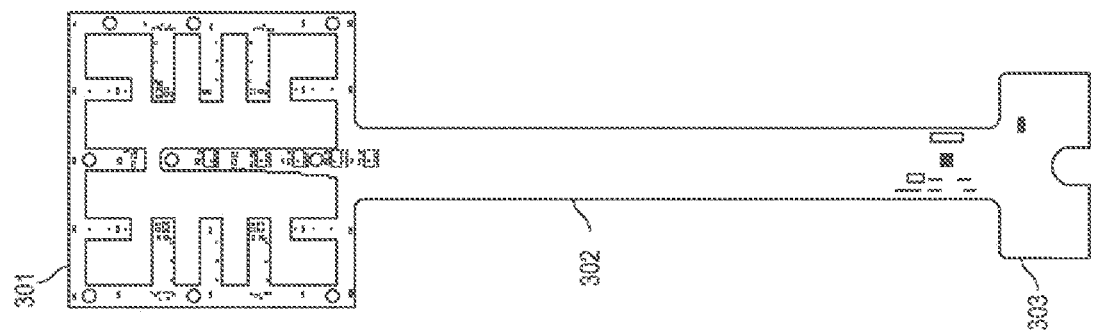
Figure 3C:
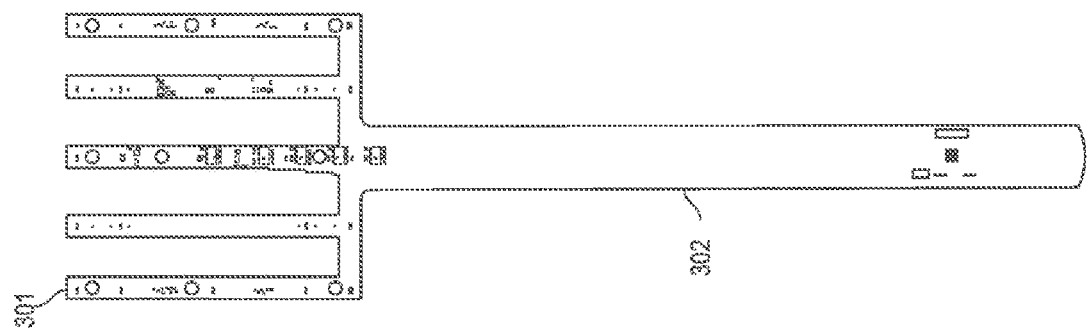

FIGS. 3C-3F show embodiments of the FPCs with four different sensor array geometries. The four different sensor array geometries shown are implemented in flexible circuits. While FIGS. 3C-3F show four different sensor array formats and configurations, the design as shown in FIG. 3D also shows the connector pads end portion 303. However, the designs of FIGS. 3C, 3E, and 3F can also be created with the connector pads end portion 303 to allow these FPC to communicate with a control module or other processing unit. FIG. 3C-3F illustrate four different sensor array geometries in the sensor array portion 301.

Figure 3G:
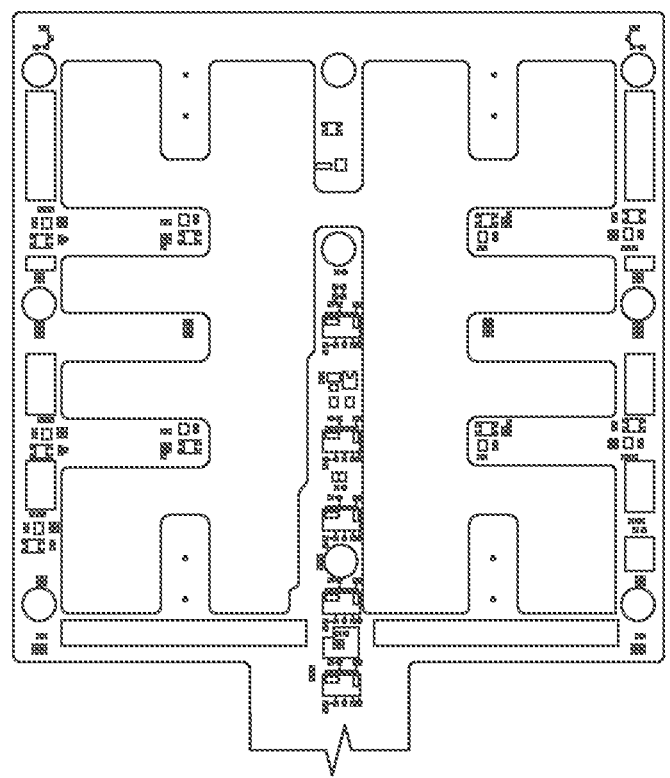
FIG. 3G shows an embodiment of the sensor array portion 301 of the sensor array design shown in FIG. 3D in more detail.
Figure 3H:
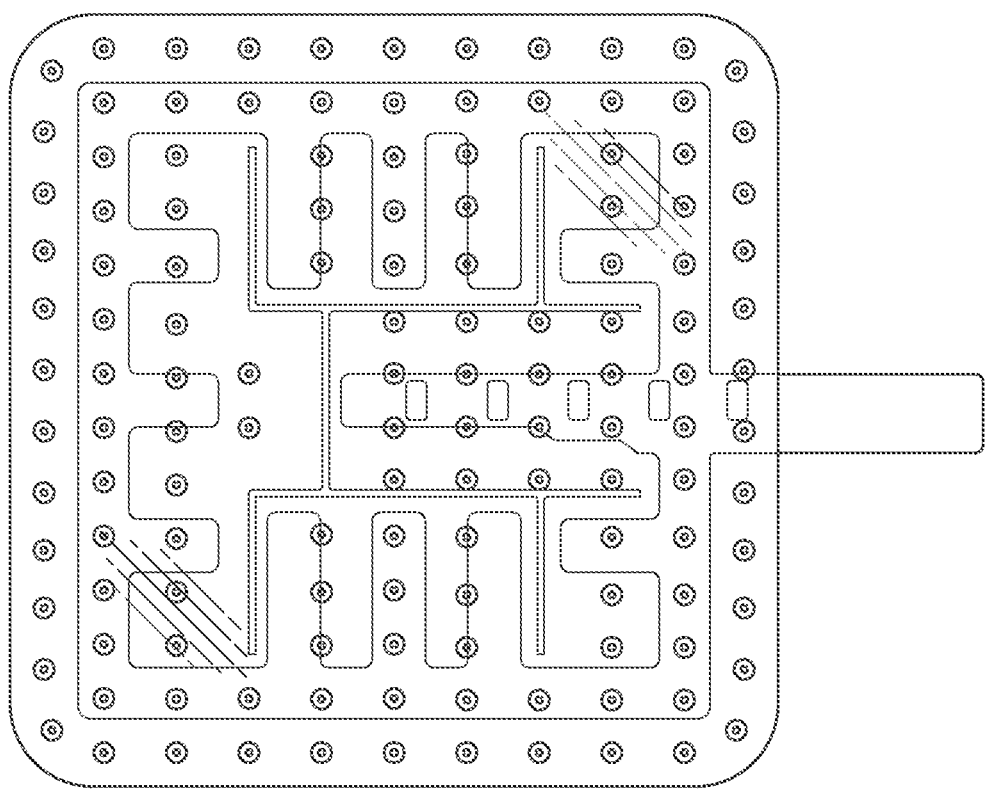
FIG. 3H illustrates a flexible sensor array incorporated into a perforated wound contact layer according to some embodiments.

FIG. 3G shows the sensor array portion 301 of the sensor array design shown in FIG. 3D in more detail according to some embodiments. In the embodiments of FIGS. 3A-3G, it will be appreciated that the sensor array portion 301 includes a plurality of portions that extend either around a perimeter of a wound dressing component such as a wound contact layer, or inward from an outer edge of the wound dressing component. For example, the embodiments illustrated include a plurality of linearly extending portions that may be parallel to edges of a wound dressing component, and in some embodiments, follow the entire perimeter of the wound dressing component. In some embodiments, the sensor array portion may comprise a first plurality of parallel linearly extending portions that are perpendicular to a second plurality of parallel linearly extending portions. These linearly extending portions may also have different lengths and may extend inward to different locations within an interior of a wound dressing component. In some embodiments, the sensor array portion does not cover the entire wound dressing component, so that gaps are formed between portions of the sensor array. As shown in FIG. 3A, this allows some, and possibly a majority of the wound dressing component to be uncovered by the sensor array. For example, for a perforated wound contact layer as shown in FIGS. 3A and 3H, the sensor array portion 301 may not block a majority of the perforations in the wound contact layer. In some embodiments, the sensor array may also be perforated or shaped to match the perforations in the wound contact layer to minimize the blocking of perforations to fluid flow.

Electrical or electronic connectivity for the sensor array can vary depending on the various sensors and sensor array designs utilized. In some embodiments, as shown in FIG. 3C-3F, a total of 79 connections can be used to connect the components of the sensor array. For example, a subset or entirety of sensors with in the sensor array can be connected with each other. The sensor arrays can be terminated in two parallel 40-way 0.5 mm pitch Flat Flexible Cable (FFC) contact surfaces, with terminals on the top surface, designed to be connected to an FFC connector such as Molex 54104-4031.

In some embodiments, temperature sensors, conductivity sensors, SpO2 sensors, or optical, ultraviolet (UV), infrared (IR), or other type of visible or invisible light sensors can be used on the sensor array to provide information relating to conditions of the wound. Optical, ultraviolet (UV), infrared (IR), or other type of visible or invisible light or other electromagnetic spectrum sensors can provide spectral measurement(s) of the wound. The sensor array and individual sensors can assist a clinician in monitoring the healing of the wound. The one or more sensors can operate individually or in coordination with each other to provide data relating to the wound and wound healing characteristics.

Temperature sensors or thermometers can use thermocouples or thermistors to measure temperature. Temperature sensors can be used to measure or track the temperature of the underlying wound or the thermal environment within the wound dressing. Temperatures sensors can be calibrated and the data obtained from the sensors can be processed to provide information about the wound environment In some embodiments, a second temperature sensor measuring temperature of another region that is different from the region of interest or an ambient sensor measuring ambient air temperature can also be used to assist in eliminating problems associated with environment temperature shifts, such as to compensate for heat flux changes away from the region of interest or compensate for physiological effects associated with ambient temperature changes.

Optical sensors can be used to measure wound or skin parameters, such as appearance of one or more of wound tissue, exudate, wound site, or skin surrounding the wound, using a light sensor (for example, optical, ultraviolet (UV), infrared (IR), or other type of visible or invisible light sensor) with an integrated or separate illumination source. In some embodiments, the sensor (along with a separate illumination source where used) can be pressed up against the skin, such that light would penetrate into the tissue and take on the spectral features of the tissue itself. In some implementations, the sensor (along with a separate illumination source where used) can be positioned remote or distant from an imaging region. A light guide, such as silicone, or optical fibers can be used to transmit light onto the imaging region. Optical sensors can measure one or more of the surface or components (such as tissue, vessels, etc.) at various depths below the surface. Diffusion of light at one or more wavelengths can be used to obtain measurements at various depths (such as, to gain depth accuracy or selectivity). Measurements at various depths can be performed by changing or varying spacing between light sources and detectors. Optical coherence tomography can be used to obtain depth information. Confocal techniques can be used to gain depth accuracy or selectivity. Optical sensors can be used to measure gloss or polarization of the wound, which can be used to measure exudate levels, presence of biofilms, etc. One or more optical features, such as waveguides, lenses, or polarizing features, can be incorporated into or under the wound dressing to assist with measurements (such as, depth measurements). For example, one or more polarizing features can be incorporated into or under a biocompatible dressing layer to enable or enhance polarization measurements, which may be used for depth measurements or blood perfusion or oxygen saturation measurements.

In some embodiments, one or more optical fingerprint sensors can be utilized. Such sensors can act as spectroscopy devices and can be configured to measure the presence of absence of a certain spectral response. The response can be liner or non-linear (fluorescence). For example, florescence measurements can include exudate measurements, tissue fluorescence (such as by contact measurements), or bacterial fluorescence. Presence or absence of one or more compounds, such as volatile organic compounds (VOCs), can be identified from the spectral response. Presence of compounds can indicate metabolic, biological, or chemical activity that may be associated with, for example, infection or normal healing process. Presence or absence of specific molecules can be identified from the spectral response. For instance, presence of ozone (which can be beneficial for wound healing) can be identified in the spectral region of about 220 nm to about 330 nm. Infrared spectral measurements can be used to identify presence of carboxylic acids (such as, butylitic acid), which can be associated with proteins. In certain implementations, one or more biomarkers or dyes can be used to enhance spectral visibility or response of one or more components of interest.

In some implementations, one or more optical sources or detectors can be positioned outside of the wound. The wound can be illuminated or light can be detected through the tissue. Transillumination can be used to identify presence of absence of abnormalities.

In certain cases, one or more electronic nose (or e-nose) sensors can be used to detect presence of one or more VOCs.

Light propagation in tissue can be dominated by two major phenomena, scattering and attenuation. For attenuation, as light passes through tissue, its intensity may be lost due to absorption by various components of the tissue. Blue light tends to be attenuated heavily, whilst light at the red end of the spectrum tends to be attenuated least.

Scattering processes can be more complex, and can have various "regimes" which must be considered. The first aspect of scattering is based on the size of the scattering centre compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart—so a 1 mm path distance would effectively randomise the photon direction and the system would enter a diffusive regime.

Figure 3I:
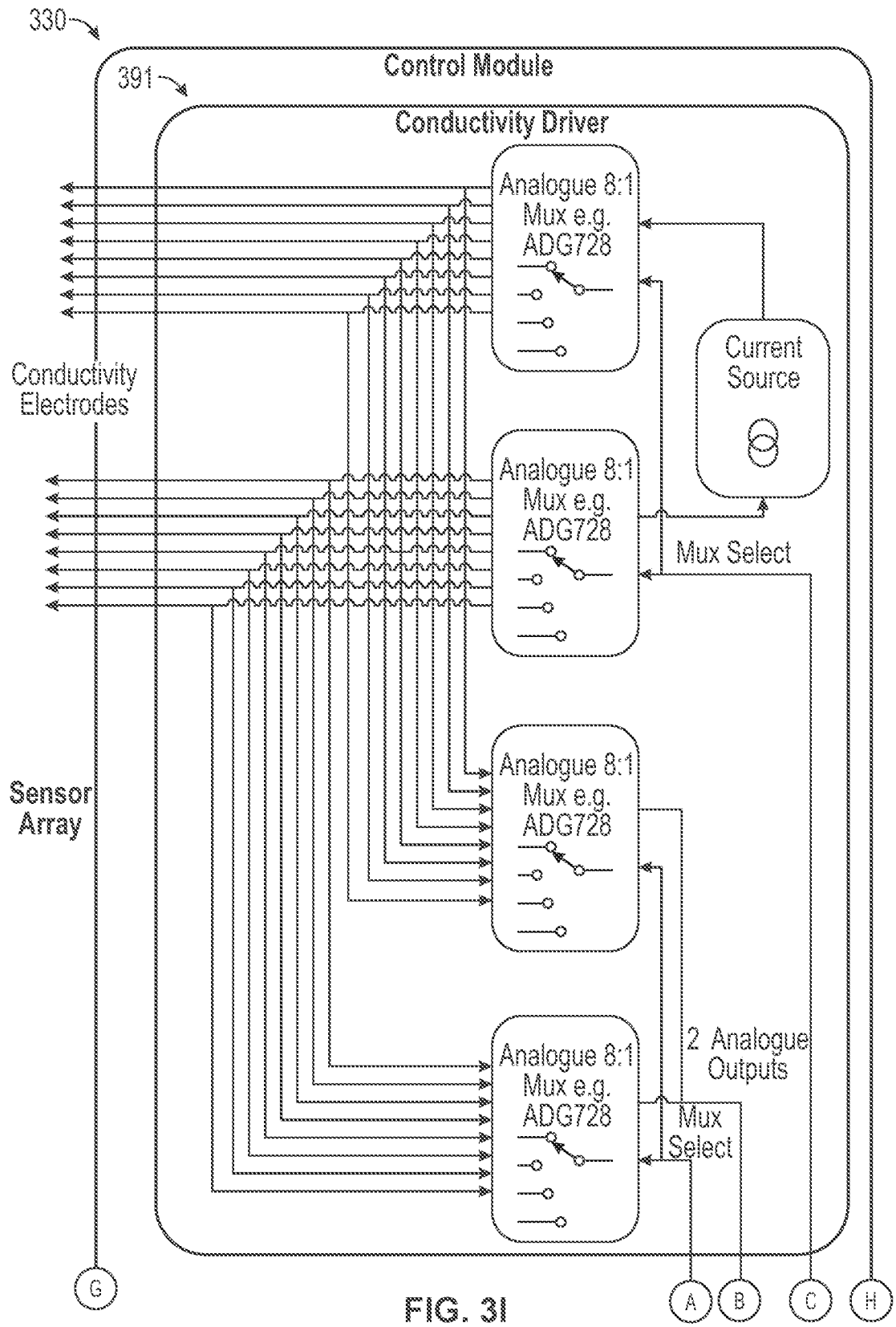
FIG. 3I illustrates a control module according to some embodiments.
Figure 3I:
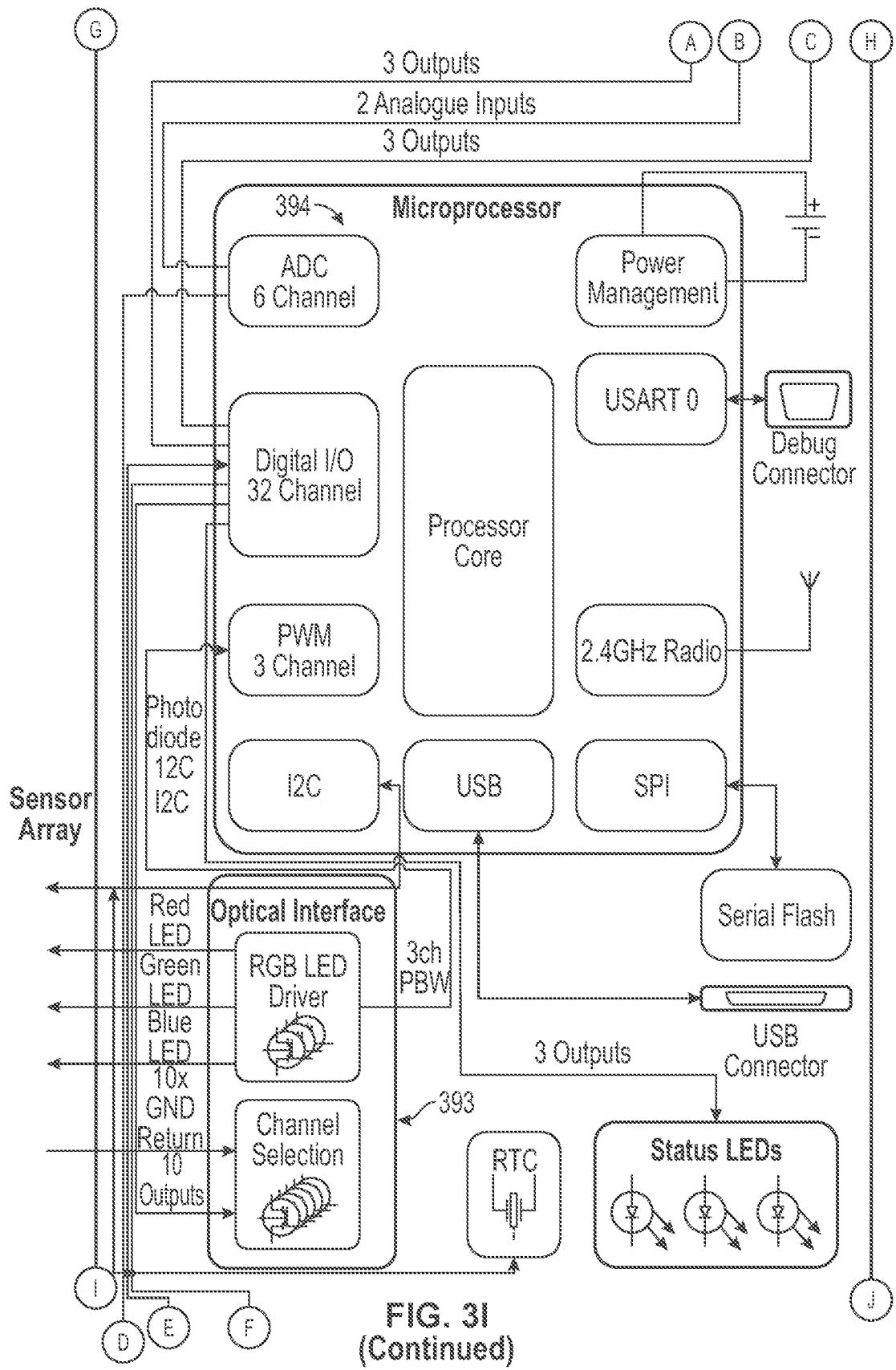
Figure 3I:
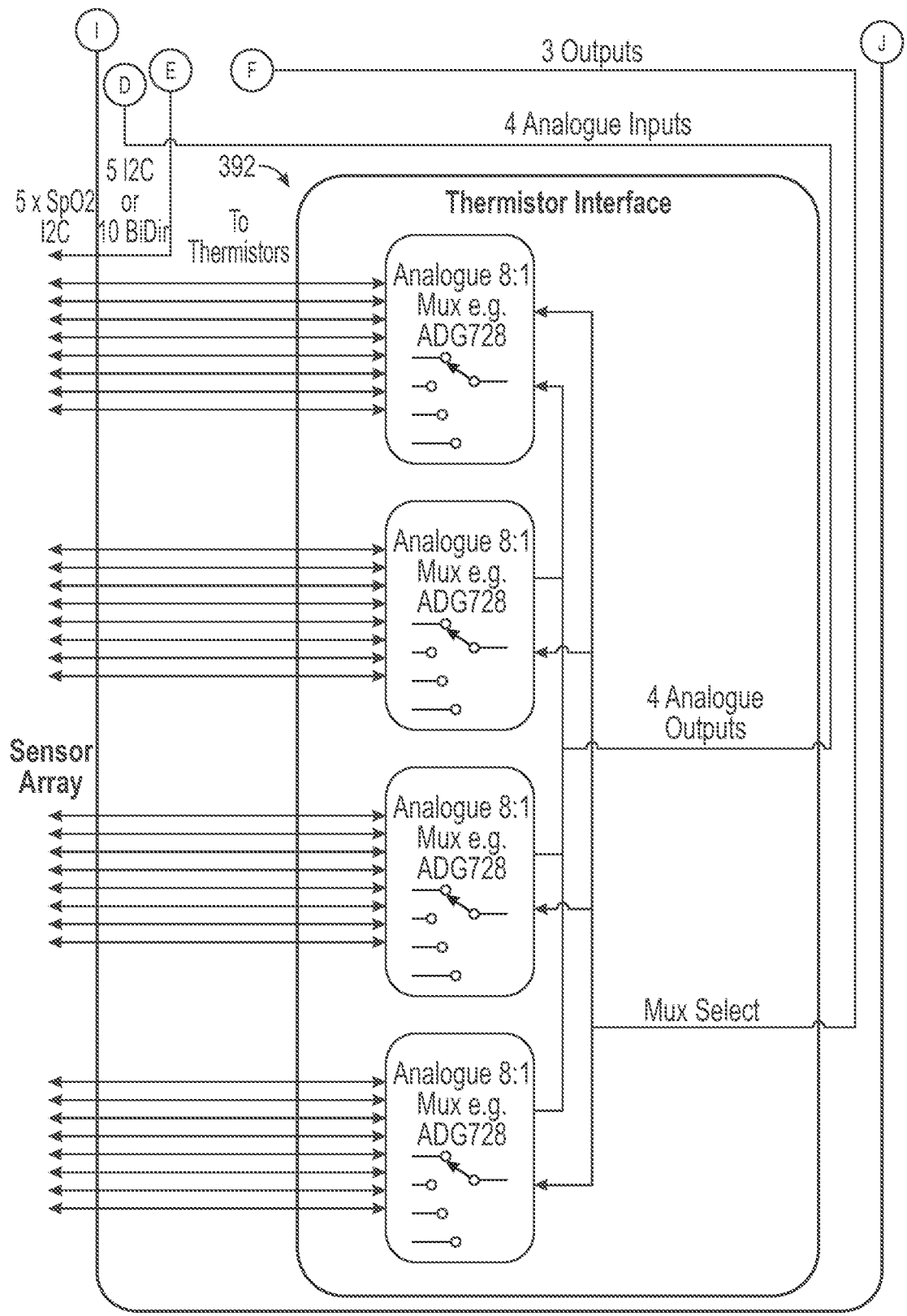
Figure 3J:
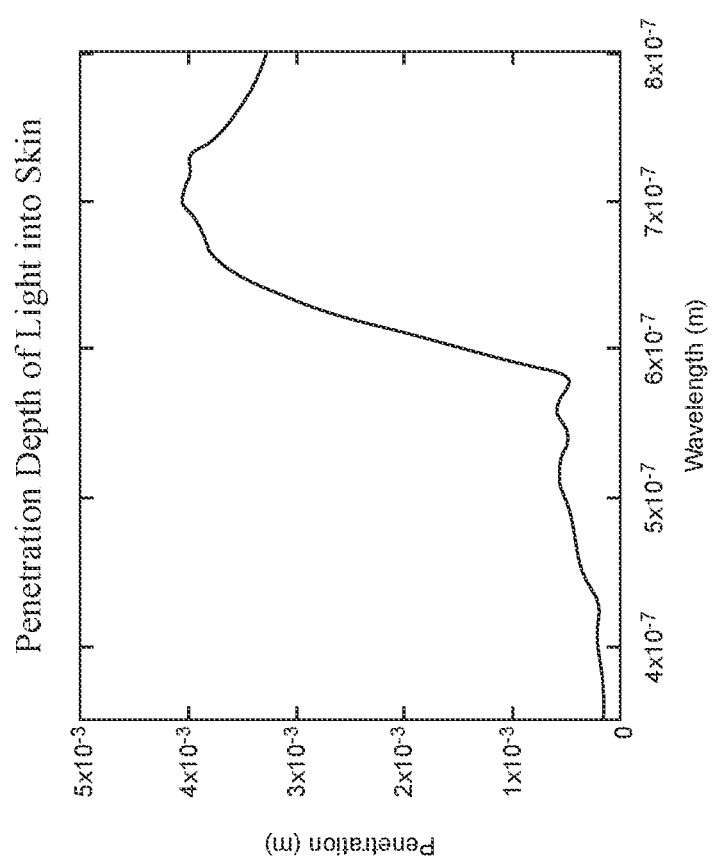
FIGS. 3J-3K show the results of optical sensors used on tissue and the scattering and the attenuation of light into tissue according to some embodiments.
Figure 3K:
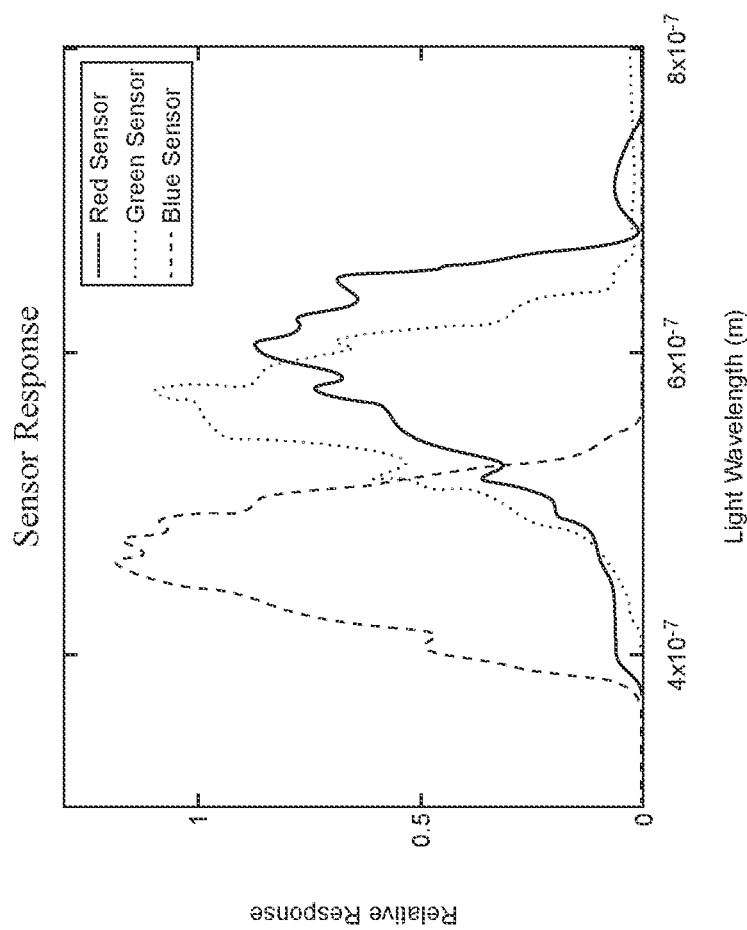

FIG. 3J shows how far light can pass through the skin before its intensity is attenuated by a factor of l/e (which is around 37% of its original intensity) according to some embodiments. The intensity loss is an exponential function (the Beer-Lambert law) given by:

$$I(x) = I_0 e^{-x\mu(\lambda)}$$

Where $\mu$ is the value of the penetration depth. This exponential fall in intensity is the reason why tissue appears red when illuminated—almost all light which propagates into and out of the tissue will be in the red end of the spectrum. This can be thought of as a filter, which varies with distance in how it behaves—as a source of light is moved further away, the spectrum reaching the detector will change accordingly. The graph of FIGS. 3J and 3K is a combination of factors—the scattering and the attenuation of light into tissue. FIG. 3J shows the intensity loss of light into tissue. FIG. 3K shows the response of the optical detector according to some embodiments.

Figure 3L:
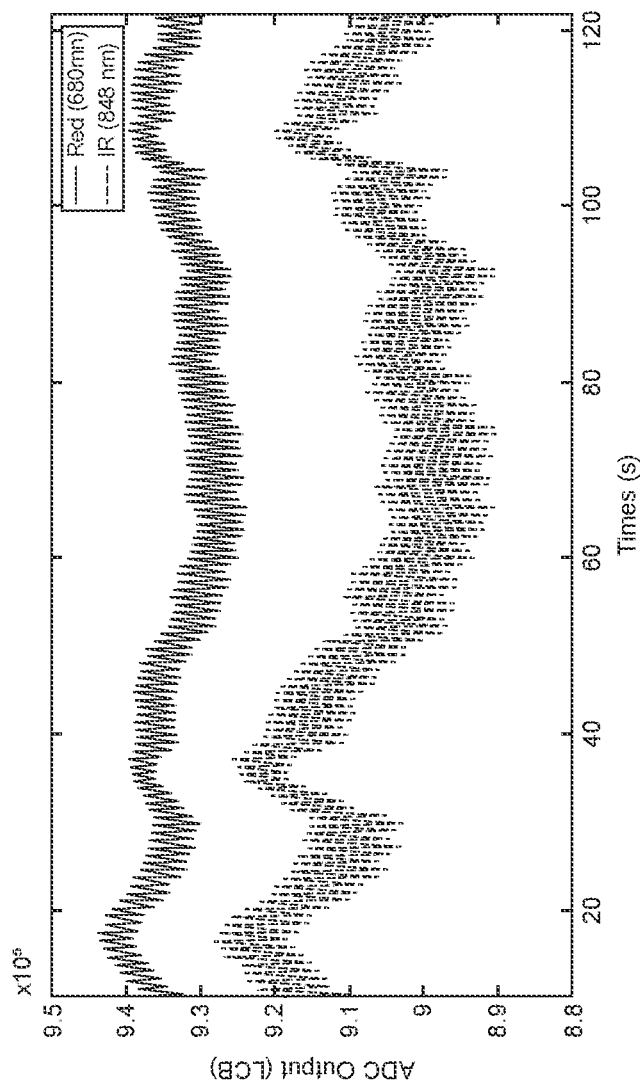
FIGS. 3L-3M show a measurement taken using an SpO2 sensor in its raw form according to some embodiments.
Figure 3M:
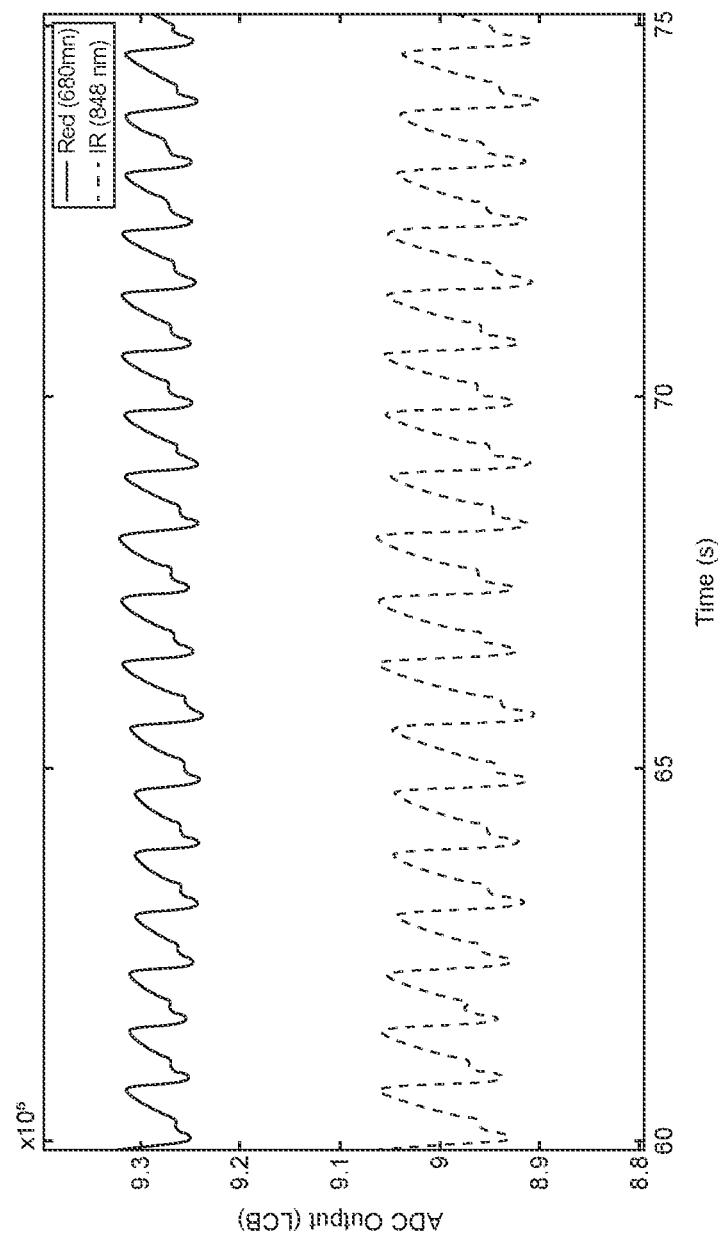

Suitable light sources, such as ultrabright light emitting diodes (LEDs), an optical detectors, or polyester optical filters can be used as components of the optical sensors to measure through optical properties of the tissue, exudate, or foreign bodies (such as, for tissue color differentiation). For example, because surface color can be measured from reflected light, a color can be measured from light which has passed through the tissue first for a given geometry. This can include color sensing from diffuse scattered light, from a light source (such as, white, RGB, IR LED, or the like) in contact with the wound or skin. In some embodiments, a light source can be used with an optical detector nearby to detect the light which has diffused through the tissue. The optical sensors can image with diffuse internal light or surface reflected light. A suitable optical detector, such as a photodiode, can be used. For example, an optical detector can have a red, green, blue, clear (RGBC) spectral response (or sensitivity ratios on the channels) as illustrated in FIG. 3Q. In some cases, a Rhom BH1745NUC color sensor can be used.

Additionally, the optical sensors can be used to measure autofluorescence. Autoflourescense is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

Conductivity or impedance sensors can be used to determine the difference between living and dead tissue or to show a change in impedance due to a wound being opened up in morbid tissue. Conductivity sensors can include Ag/AgCl electrodes and an impedance analyser. The conductivity sensors can be used to measure the change of impedance of a region of wound growth by measuring the impedance of the surrounding tissue/area. In some embodiments, the sensor array can utilize conductivity sensors to measure the change in conductivity on perimeter electrodes due to a wound size or wound shape change. For example, tomographic reconstruction or techniques can be used to infer wound size by using different spacing of conductivity sensors or electrodes. Voltage or current probes can be used to apply voltage or current stimuli to determine or test patient's nerve responses or to promote wound healing. In some embodiments, the conductivity sensors can be used in the wound bed or on the perimeter of the wound. Conductivity measurements can be used to detect adherence failure of the dressing. Conductivity can be measured through a conductive path that goes through a biocompatible layer (for example, of the wound dressing) or through a biocompatible gel layer (for example, conductive gel layer) or saline solution to contact the wound. Measurements can be made in a frequency range of about 2.5 kHz to about 60 kHz. This can be similar to using large patch clamp measurements. Alternatively or additionally, conductivity can be measured using capacitance or a capacitive-coupling method without forming direct contact with the tissue (for example, using non-contact electrodes). For example, transmission in the frequency range of about 30 kHz to about 70 kHz can be used. Conductivity can be measured using three point probe measurement or four point probe measurement. Conductivity of one or more of wound tissue or exudate can be measured, which can be used to infer cell or tissue health. Conductivity of a region around a wound (such as, skin or tissue surrounding the wound) can be measured. Conductivity sensors can be retractable to move in out as needed. Conductivity sensors can include fine or micro probe needles with conductive tips which extend into the wound and insulating shafts. Conductivity sensors can be dangling probes under a wound contact layer, which come into contact with the wound. Conductivity sensors can include dry contact electrodes. Conductivity sensors can include electrodes that are configured to ensure or promote biocompatibility, such as gold, silver, platinum, or carbon electrodes.

In some embodiments, pH changing pads can be used as a pH sensor. A spectrometer and a broadband white light source or RGB LED can be used to measure the spectral response of the pH dye. The illumination and imaging can be provided on the surface of the wound dressing that is in contact with the wound and at the same side as the fluid application, the bottom surface. Alternatively, in some embodiments, the illumination and imaging source can be provided on the surface of the wound dressing opposite the bottom surface and away from fluid application or the top surface of the dressing or wound contact layer. In some implementations, a pH sensor is an optical measurement device that includes two or three (or less or more) wavelengths of light being measured spectrally as light reflects off a colorimetric substance. A pH-changing foam can be included or integrated into the wound dressing. The foam can change spectral absorption of light depending on the environment (for example, depending on the contents or composition of wound exudate). Alternatively or additionally, a pad or feature that changes in color due to pH alterations in the environment can be utilized. Such pad can be optically measured and assessed to determine pH levels. In certain cases, a pH sensor can include an exudate channeling system (such as a flow path) that allows for exudate to flow across sensor's pH sensitive regions, which can improve detection accuracy. In some cases, the entire or substantially entire dressing can be made pH-sensitive.

In some embodiments, one or more pulse oximetry sensors, such as SpO2 sensors, can be used. Such sensors can obtain multispectral optical measurements, which can be used, for example, to measure one or more of how oxygenated the blood is and the pulsatile blood flow. Multispectral optical measurements sensors can determine time resolved optical measurements. In some cases, pulse oximetry measurements work by taking a time resolved measurement of light absorption/transmission in tissue at two different optical wavelengths. When hemoglobin becomes oxygenated, its absorption spectrum changes with regards to non-oxygenated blood. By taking a measurement at two different wavelengths, one gains a ratio metric measure of how oxygenated the blood is. For example, SpO2 sensor(s) can operate at approximately 500 Hz sample rate and obtain dual band red (R) and infrared (IR) measurements. According to some embodiments, a measurement taken using the SpO2 sensor in its raw form is shown in FIG. 3L and FIG. 3M. FIG. 3M shows a zoomed in view of the graph of FIG. 3L according to some embodiments.

From the zoomed in graph of FIG. 3M, the waveform of pulsatile blood flow can clearly be observed. In order to extract SpO2, the value extracted from the data is the ratio between the height of a given pulse peak and its trough for each wavelength. Then, another ratio is taken between these two values. The peaks and troughs can be accurately located using a peak detection algorithm. Several points of data can be taken for each situation and averaged.

$$R = \frac{\left(\frac{A_{AC}}{A_{DC}}\right)_{Red}}{\left(\frac{A_{AC}}{A_{DC}}\right)_{IR}}$$

Once this ratio is calculated, it is empirically fit to SpO2 levels using a 'lookup table' that can be held on the hardware. This value fundamentally depends on the absorption and scattering of human tissue at each wavelength, but the complexities in modelling the system are avoid by using an empirical model.

The components in the sensor array can be connected through multiple connections. In some embodiments, the temperature sensors (such as, thermistors) can be arranged in groups of five. In some embodiments, multiple thermistors can be used with each thermistor being nominally 10 kΩ, and each group of five has a common ground. There are five groups of thermistors, giving a total of 30 connections. In some embodiments, there can be nine conductivity terminals. Each conductivity terminal requires one connection, giving a total of 9 connections. In certain implementations, at most 8 connections are used. For example, four connections can be made close to the center of the sensor array (such as, 3 cm sided square) and four connections can be made on the periphery of the sensor array (such as, 9 cm sided square). In certain implementations, an additional conductive layer can be incorporated on the side of a conductivity pad (on which connections are formed) facing away from the tissue. The additional conductive layer can be isolated from the conductivity pad by a non-conductive layer. This can help to orient electromagnetic propagation.

In some embodiments, there can be five SpO2 sensors. In some embodiments, aach SpO2 sensor requires three connections, plus power and ground (these are covered separately), giving a total of 15 connections. In some embodiments, there can be 10 optical, UV, IR, or other type of visible or invisible light sensors. Each such sensor can comprise light source, such as an RGB LED or an RGB photodiode. Each such sensor may require six connections, however five of these are common to every sensor, giving a total of 15 connections. Power and ground are considered separately. In some embodiments, there can be 5 pH sensors. The pH sensors can be a color-change discs, and can be sensed using the optical, UV, IR, or other type of visible or invisible light sensors described above. Therefore, the pH sensors require no additional connections. There can be three power rails, and seven common return signals, giving a total of 10 common connections. In some embodiments, the sensor array can include 25 temperature sensors (such as, thermistors Murata NCP15WB473E03RC), 9 conductivity terminals, 5 SpO2 sensors (for instance, ADPD144RI), 10 light sources (for example, RGB LEDs such as KPTF-1616RGBC-13), 10 Optical, UV, IR, or other type of visible or invisible light Sensors, 10 FET, a printed circuit board (PCB), and an assembly.

FIG. 3H illustrates a flexible sensor array incorporated into a perforated wound contact layer according to some embodiments. As shown in FIG. 3H, the PCB sensor array can be sandwiched between two films or wound contact layers. The wound contact layers can have perforations formed as slits or holes as described herein that are small enough to help prevent tissue ingrowth into the wound dressing while allowing wound exudate to flow into the dressing. In some embodiments, the wound contact layers can have one or more slits that increase flexibility of the wound contact layer with integrated sensor array. In some embodiments, one of the wound contact layers can have extra cut outs to accommodate the sensors so that they can contact the skin directly.

In some embodiments, circuits are placed or printed onto one side of a substrate and electronic components, such as sensors, are also placed on that side. The components and tracks can then be covered with one or more layers of insulation or encapsulant on one or both sides of the substrate.

Figure 3N:
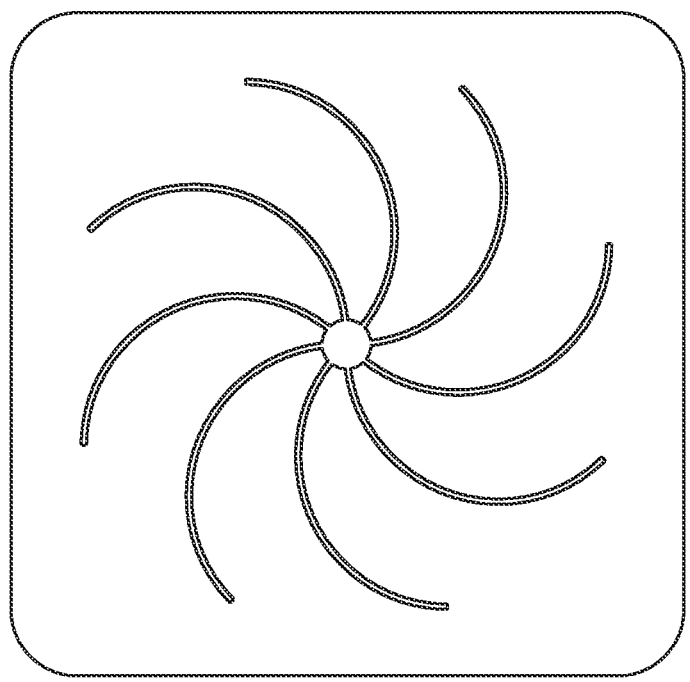
FIG. 3N illustrates a wound contact layer including holes and curved slits extending radially from a central hole according to some embodiments.
Figure 30:
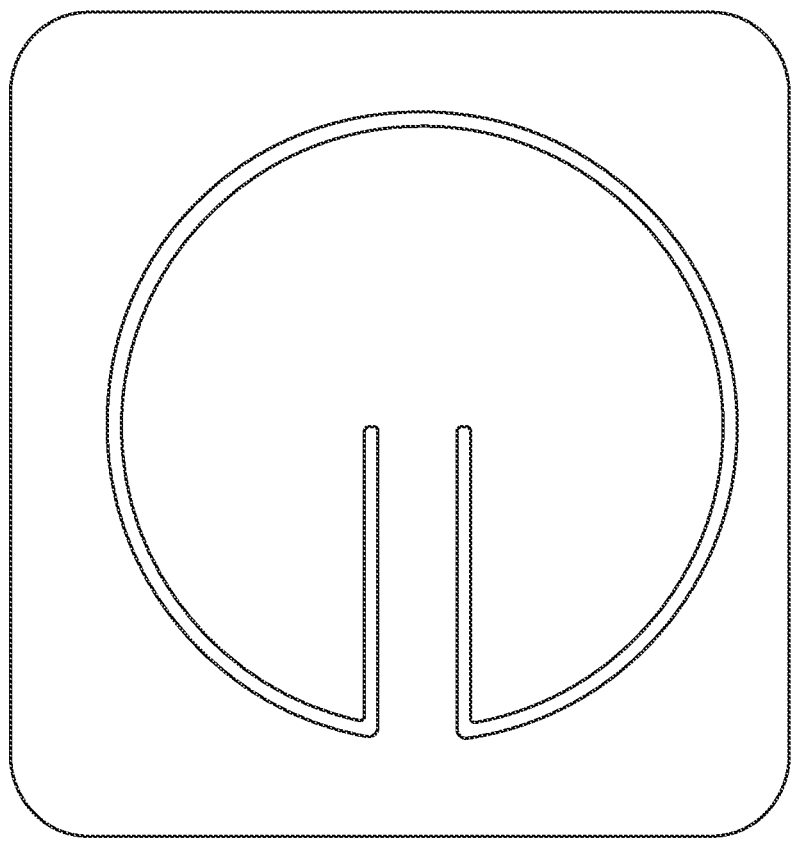
Figure 3P:
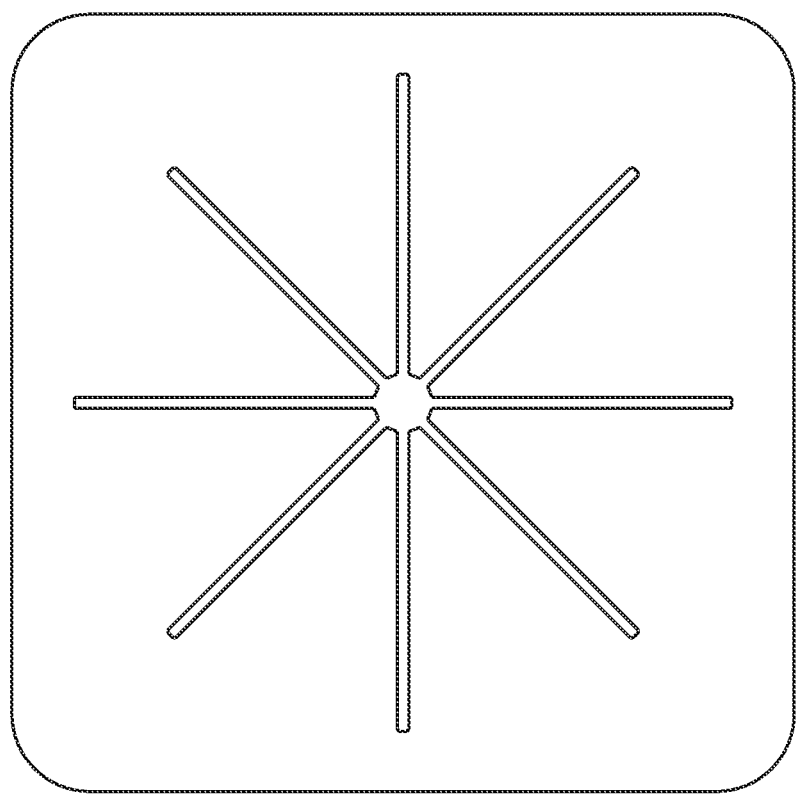
FIG. 3P illustrates a wound contact layer including holes and slits extending radially from a central hole according to some embodiments.
Figure 3Q:
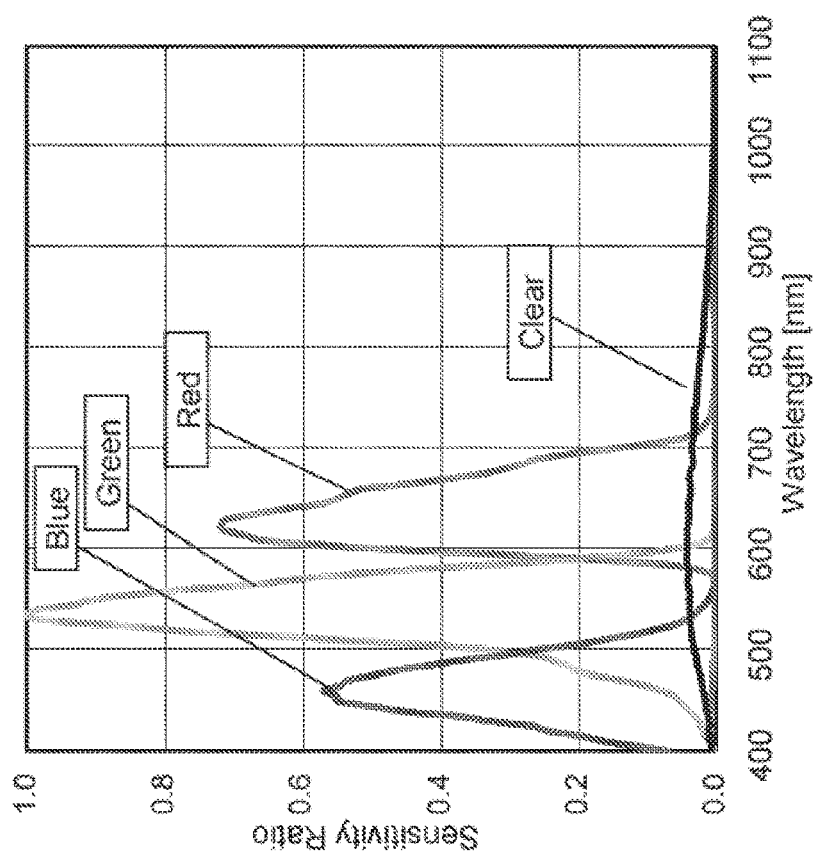
FIG. 3Q illustrates spectral response of an optical detector according to some embodiments.

FIGS. 3N-3P illustrates a wound contact layer comprising slits and holes in various arrangements to increase flexibility, allow the sensors to access the wound are directly, and assist in the transport of fluid through the wound contact layer. In some embodiments, the arrangement of the holes and slits can allow the sensors to access to the center of the wound, edges of the wound, or the intact skin. FIGS. 3N-3P illustrate embodiments of wound contact layer with various slit arrangements and configurations. FIG. 3N illustrates embodiments of a wound contact layer including holes and curved slits extending radially from a large central hole.

FIG. 3O illustrates a wound contact layer including holes and curved slits forming a partial circle and slits that extend from the perimeter of the circle to the center of the wound contact layer according to some embodiments.

FIG. 3P illustrate a wound contact layer including holes and slits extending radially from a large central hole toward the outer perimeter of the wound contact layer according to some embodiments.

A controller or control module can be used to interface with the sensor array. In some embodiments, the control module can contain a power source, such as batteries, and electronics to drive the sensors. The control module can also log data at appropriate intervals and allow data transfer to an external computing device, such as a personal computer (PC). The control module can be customized to have various features depending on the sensors used in the sensor array and the data collected by the sensors. In some embodiments, the control module can be comfortable enough and small enough to be worn continuously for several weeks. In some embodiments, the control module can be positioned near the wound dressing or on the wound dressing. In some embodiments, the control module can be positioned in a remote location from the wound dressing and accompanying sensor array. The control module can communicate with the sensor array and wound dressing through electrical wires or through wireless communication whether positioned on the dressing, near the dressing, or remote from the wound dressing. Wireless communication can be performed using one or more frequency bands of 125 kHz to 134 kHz, 13.56 MHz, 784 MHz, 856 MHz to 960 MHz, 868 Mhz, 915 Mhz, 2400 MHz to 2483.5 Mhz, 3.6 GHz, 4.9 GHz, 5 GHz, or 5.9 GHz. In some embodiments, the control module can be adapted to be utilized with different sensor arrays and can enable easy replacement of the sensor array.

In some implementations, the control module or electronics to which the sensor array is connected can include additional sensors. As another example, one or more additional sensors can detect blood sugar or glucose levels, hydration, or other physiological parameters (for example, comorbidities, nutritional status, treatments, timescales, general status of a patient). One or more hydration sensors can perform an inductive measurement with alternating current (AC) across two pads and a voltage measurement across two other pads. Additionally or alternatively, skin elasticity can be correlated with nutritional status or hydration. Skin elasticity can be determined by performing an ultrasound sweep at a shallow penetration. An elastomeric electroactive polymer or another piezoelectric transducer can be used as a transducer or receiver for performing the ultrasound sweep.

Data collected by one or more additional sensors can be used to correlate data received from the sensor array in order to test or improve accuracy. In some embodiments, variations in the output of one or more sensors in the sensor array that matches the range of pulsatile blood flow (such as, about 0.3 Hz to about 4 Hz) can be determined and correlated with data collected by one or more additional sensors. This can be used for testing or improving accuracy of the sensor array.

In some embodiments, the control module can include various requirements and combination of features including but not limited to the features listed in Table 1 below.

TABLE 1

| OPTIONAL FEATURES FOR CONTROL MODULE |
| --- |
| 7 day operation from a single set of batteries |
| 28 day local, non-volatile, storage capacity |
| Easy to charge, or to replace battery |
| Wireless link to PC/tablet (such as Bluetooth) |
| Wired link to PC (optional, micro-USB) |
| Drive electronics for temperature sensors (such as, thermistors) |
| Drive electronics for conductivity sensors |
| Drive electronics for optical sensors |
| Drive electronics for SpO2 sensors |
| Power management |
| Real Time Clock (RTC) to allow accurate data logging, and correlation with other measurands |
| Ability to change sample rates and intervals (useful for SpO2) for each sensor |
| Indication of status visually, audibly, tangibly, or the like. For example, via LED, such as (Green: Awake; Flashing green: Charging; Blue: Wireless link established; Flashing blue: Wireless data transfer; Yellow: Wired link established; Flashing yellow: Wired data transfer; Red: Battery low; Flashing red: Battery very low |

FIG. 3I illustrates a block diagram of a control module according to some embodiments. The block diagram of the control module includes a conductivity driver box 391 displaying features of the conductivity driver. Box 392 shows the features of the temperature sensor (e.g. thermistor) interface and box 393 shows the features of the optical interface. The control module can include a controller or microprocessor with features similar to those shown in box 394. Real time clock (RTC), Status LEDs, USB connector, Serial Flash, and Debug Connector can be included as features of the control module as shown in FIG. 3I.

In some embodiments, the microprocessor can have one or more of the following features: 2.4 GHz or another frequency band disclosed herein or any other suitable frequency radio (either integrated, or external); Supplied Bluetooth software stack; SPI interface; USB (or UART for external USB driver); I2C; 3 channel PWM; 32 GPIO; or 6-channel ADC. In some embodiments, the device can include at least 48 I/O pins or possibly more due to banking limitations. Bluetooth stack typically requires ~20 kB onboard Flash, so a minimum of 32 kB can be required. In some embodiment, 64 kB can be required if complex data processing is considered. The processor core can be ARM Cortex M4 or a similar processor core. In some embodiments, the parts can include ST's STM32L433LC or STM32F302R8 microprocessor, which can require an external radio, or NXP's Kinetis KW range including integrated radio.

In some embodiment, the control module can include a memory component where the amount of local storage depends on the sample rate and resolution of the sensors. For example, an estimated data requirement of 256 Mb (32 MB) can be met by using a serial Flash device from a number of manufacturers (Micron, Spansion).

The control module can utilize one or more analogue switches. In some embodiments, analogue switches with good on resistance and reasonable bandwidth can be used. For example, Analog Devices' ADG72 or NXP's NX3L4051HR can be used. In some cases, 8 of these switches may be required.

The control module can incorporate a power source, such as a battery. For example a 300 mWh/day battery can be used. For 7 days this is 2100 mWh. This could be provided by: a 10 days, non-rechargeable, ER14250 (14.5 mm diameter×25 mm) LiSOCl2 cell: or a 7 days, rechargeable, Li 14500 (14.5 mm diameter×500 mm) Li-Ion. In some embodiments, a power source separate from the control module can be used.

The control module can incorporate a real time clock (RTC). The RTC can be chosen from any RTC devices with crystal. The control module can also include miscellaneous resistors, capacitors, connectors, charge controllers, and other power supplies.

The PCB of the control module can be a 4-layer board, approximately 50 mm×20 mm, or 25 mm×40 mm. The type of PCB used can be largely driven by connection requirements to sensor array.

The enclosure of the control module can be a two part moulding, with clip features to allow easy access for changing sensor arrays or batteries.

The data collected through the sensor array can be passed through the control module and processed by a host software. The software may be executed on a processing device. The processing device can be a PC, tablet format computing device or a tablet, smartphone, or other computer capable of running host software (for example, a custom made computing device). The processing device executing the software can be in communication with the control module through electrical wires or through wireless communication. In some embodiments, the software may be configured to provide access to the data held on the control module, but not to perform big-data analysis (or edge computing) on the data received from the sensors. The host software can include an interface to the control module via Bluetooth or USB. In some embodiments, the host software can read the status of control module, download logged data from control module, upload sample rate control to control module, convert data from control module into format suitable for processing by big-data analysis engine, or upload data to cloud for processing by analysis engine.

The software may be developed for PC (Windows/Linux), tablet or smartphone (Android/iOS), or for multiple platforms. In some embodiments, data collected through the sensor array can be communicated to a remote computing device for processing. For example, data can be uploaded to the Internet or processed by the cloud. In some implementations, when the connection between the sensor array and the control module is wired, the control module can communicate with the remote computing device, such as the cloud. In certain implementations, when the connection between the sensor array and the control module is wireless, the sensor array can directly communicate with the remote computing device, such as the cloud, or use the control module to communicate with the remote computing device.

In some embodiments, electronics, including one or more of sensors or control module, can be constructed to be compatible or safe for x-ray, MRI, or other type of scanning. Electronics can be constructed to be compatible or safe with external or implantable defibrillators. Electronics can include protection against radiofrequency interference (RFI) or electromagnetic interference (EMI). For example, one or more EMI shields can be used, which can be made out of ferrite, copper, or another material. Faraday cages, or the like.

In certain implementations, security measures can be implemented to prevent measurements and other data from being accessed by unauthorized personnel. For example, certain communications or commands may be required to be transmitted over a wired interface, not wirelessly. Encryption or modulation of data can be additionally or alternatively used. In certain implementations, only a device ID, a clock time (that may not correlated with real-time clock), or raw data is provided or identified over an unsecure interface. Such data is anonymous and not meaningful without a baseline patient identification or real time clock information, which may only be provided over a secure interface.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, or adjacent to the backing layer. In some embodiments, the wound dressing can include a second cover layer or a second filter layer for positioning over the layers of the wound dressing and any of the integrated components. The second cover layer can be the upper most layer of the dressing or can be a separate envelope that enclosed the integrated components of the topical negative pressure system.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

Use of NPWT System

Figure 4A:
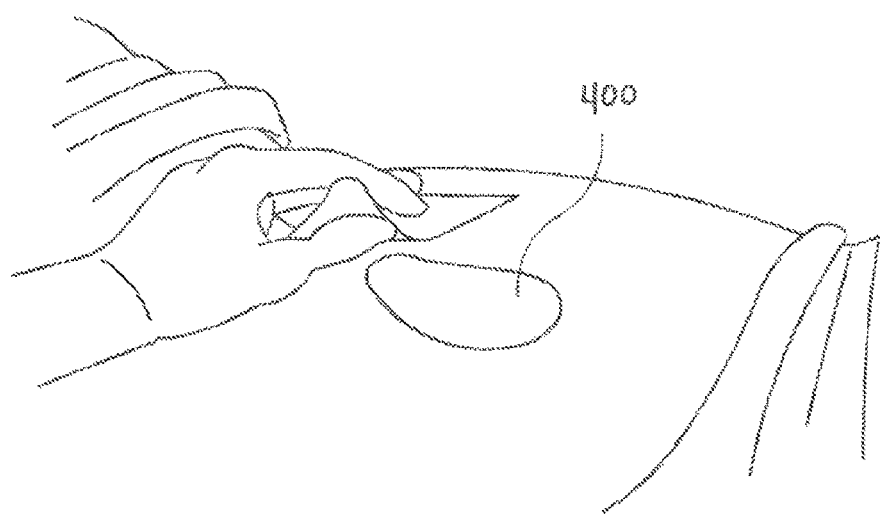
FIGS. 4A-D illustrate the use and application of a wound treatment system onto a patient according to some embodiments.

FIGS. 4A-D illustrate the use a negative pressure therapy wound treatment system being used to treat a wound site on a patient according to some embodiments. FIG. 4A shows a wound site 400 being cleaned and prepared for treatment.

Here, the healthy skin surrounding the wound site 400 can be cleaned and excess hair removed or shaved. The wound site 400 may also be irrigated with sterile saline solution if necessary. Optionally, a skin protectant may be applied to the skin surrounding the wound site 400. If necessary, a wound packing material, such as foam or gauze, may be placed in the wound site 400. This may be preferable if the wound site 400 is a deeper wound.

Figure 4B:
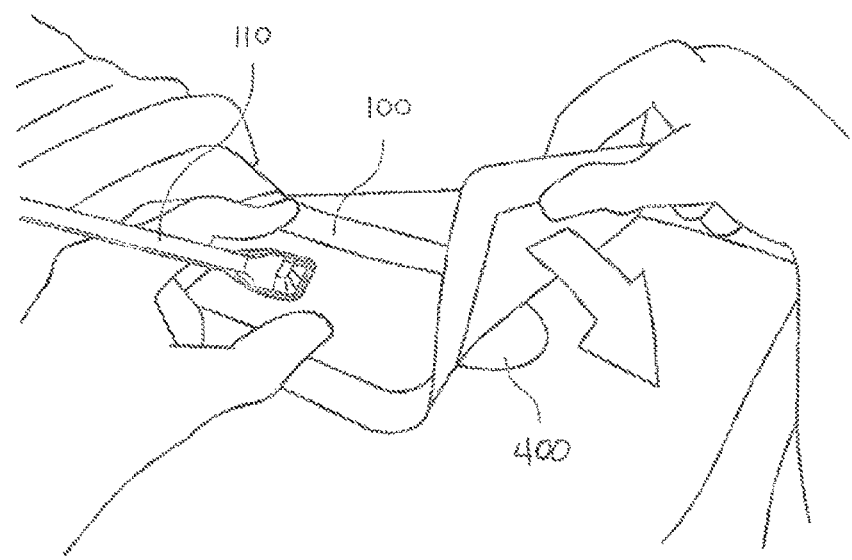

After the skin surrounding the wound site 400 is dry, and with reference now to FIG. 4B, the wound dressing 100 may be positioned and placed over the wound site 400. In some embodiments, the wound dressing 100 is placed with the wound contact layer over or in contact with the wound site 400. In some embodiments, an adhesive layer is provided on the lower surface of the wound contact layer, which may in some cases be protected by an optional release layer to be removed prior to placement of the wound dressing 100 over the wound site 400. The dressing 100 can be positioned such that the fluidic connector 110 is in a raised position with respect to the remainder of the dressing 10 so as to avoid fluid pooling around the port. In some embodiments, the dressing 100 is positioned so that the fluidic connector 110 is not directly overlying the wound, and is level with or at a higher point than the wound. To help ensure adequate sealing for TNP, the edges of the dressing 100 can be smoothed over to avoid creases or folds.

Figure 4C:
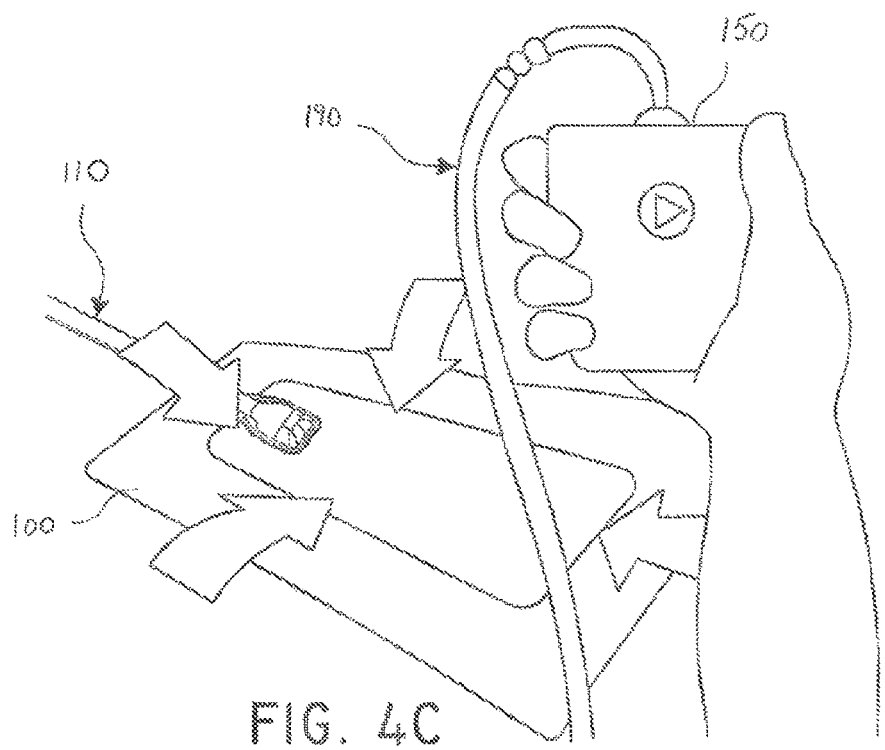

With reference now to FIG. 4C, the dressing 10 is connected to the pump 150. The pump 150 is configured to apply negative pressure to the wound site via the dressing 100, and typically through a conduit. In some embodiments, and as described herein, a fluidic connector 110 may be used to join the conduit 190 from the pump to the dressing 100. Where the fluidic connector is adhered to the top layer of the wound dressing, a length of tubing may be coupled at a first end of the fluidic connector such that the tubing, or conduit, extends away from the fluidic connector parallel to the top of the dressing. In some embodiments the conduit may comprise a fluidic connector. It is expressly contemplated that a conduit may be a soft bridge, a hard tube, or any other apparatus which may serve to transport fluid. Upon the application of negative pressure with the pump 150, the dressing 100 may in some embodiments partially collapse and present a wrinkled appearance as a result of the evacuation of some or all of the air underneath the dressing 100. In some embodiments, the pump 150 may be configured to detect if any leaks are present in the dressing 100, such as at the interface between the dressing 100 and the skin surrounding the wound site 400. Should a leak be found, such leak can be remedied prior to continuing treatment.

Figure 4D:
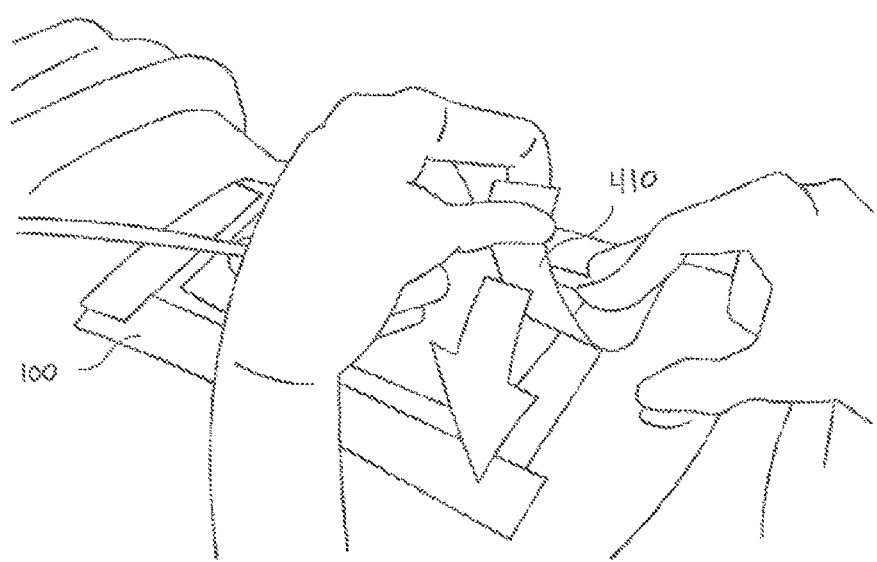

Turning to FIG. 4D, additional fixation strips 410 may also be attached around the edges of the dressing 100. Such fixation strips 410 may be advantageous in some situations so as to provide additional sealing against the skin of the patient surrounding the wound site 400. For example, the fixation strips 410 may provide additional sealing for when a patient is more mobile. In some cases, the fixation strips 410 may be used prior to activation of the pump 150, particularly if the dressing 100 is placed over a difficult to reach or contoured area.

Treatment of the wound site 400 can continue until the wound has reached a desired level of healing. In some embodiments, it may be desirable to replace the dressing 100 after a certain time period has elapsed, or if the dressing is full of wound fluids. During such changes, the pump 150 may be kept, with just the dressing 100 being changed. A similar procedure as described with reference to FIG. 4A-4D can be followed for application of the wound dressing used without negative pressure. However, the wound dressing does not comprise a port or a fluidic connector and the dressing would not be connected to a negative pressure source as described in FIG. 4C.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

All of the features disclosed in this specification (including any accompanying exhibits, claims, abstract and drawings), or all of the steps of any method or process so disclosed, may be combined in any combination, except combinations where at least some of such features or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future. The language of the claims is to be interpreted broadly based on the language employed in the claims and not limited to the examples described in the present specification or during the prosecution of the application, which examples are to be construed as non-exclusive. The scope of the present disclosure is not intended to be limited by the specific disclosures of preferred embodiments herein, and may be defined by claims as presented herein or as presented in the future.

What is claimed is:

1. A wound monitoring apparatus, comprising:
   a wound dressing configured to be positioned in contact with a wound, the wound dressing comprising at least one substantially flexible substrate supporting a plurality of sensors, wherein at least one of the plurality of sensors and the at least one substantially flexible substrate supporting the plurality of sensors are configured to be in direct contact with the wound, and
   wherein the at least one substantially flexible substrate is a substantially flexible printed circuit.

2. The apparatus of claim 1, wherein the substantially flexible printed circuit comprises a flexible polymer.

3. The apparatus of claim 1, wherein the at least one substantially flexible substrate comprises a substantially flexible non-conducting mesh.

4. The apparatus of claim 1, wherein the plurality of sensors are electrically connected with each other, the plurality of sensors further configured to be electrically connected with a controller and a power source.

5. The apparatus of claim 1, wherein the plurality of sensors comprise one or more temperature sensors, conductivity sensors, multispectral optical measurements sensors, pH sensors, pressure sensors, colorimetric sensors, optical sensors, ultraviolet (UV) sensors, or infrared (IR) sensors.

6. The apparatus of claim 1, further comprising:
   a controller in electrical communication with the plurality of sensors, the controller configured to receive data from the plurality of sensors and communicate the data to a processing device configured to use host software to process the data collected by the plurality of sensors to determine one or more conditions associated with the wound.

7. The apparatus of claim 6, wherein at least one of the controller or the processing device is configured to indicate, based on the one or more conditions associated with the wound, that the wound is healing.

8. The apparatus of claim 6, wherein the controller is configured to wirelessly communicate with at least one of the plurality of sensors or the processing device.

9. The apparatus of claim 6, wherein the controller is configured to be in electrical communication with at least one of the plurality of sensors or the processing device through electrical wiring.

10. The apparatus of claim 6, wherein the processing device comprises a personal computer (PC), a tablet format computing device, a smartphone, or a custom computing device.

11. The apparatus of claim 6, wherein the data collected by the plurality of sensors is configured to be communicated to the cloud.

12. The apparatus of claim 1, wherein the wound dressing comprises a wound contact layer and the at least one substantially flexible substrate is positioned on or in the wound contact layer.

13. The apparatus of claim 12, wherein the wound contact layer comprises a first wound contact layer and a second wound contact layer.

14. The apparatus of claim 13, wherein the at least one of the plurality of sensors is encapsulated between the first wound contact layer and the second wound contact layer.

15. The apparatus of claim 12, wherein the plurality of sensors comprises at least a first sensor configured to be in direct contact with the wound and at least a second sensor configured to not contact the wound.

16. The apparatus of claim 12, further comprising an absorbent layer positioned over the wound contact layer and a backing layer positioned over the wound contact layer, wherein the wound contact layer is sealed to the backing layer.

17. The apparatus of claim 16, further comprising a port on the backing layer, the port configured to connect the wound dressing to a source of negative pressure.

18. The apparatus of claim 1, wherein the wound dressing is included in a multi-layer wound dressing configured to treat the wound without the use of negative pressure.

19. The apparatus of claim 1, further comprising a wound packing layer and a drape that are configured to be positioned over the wound separately from the wound dressing.

20. The apparatus of claim 1, further comprising a negative pressure source configured to be in fluid communication with the wound dressing and further configured to apply negative pressure to the wound.

21. A wound monitoring apparatus, comprising:
a wound dressing configured to be positioned in contact with one or more of a wound or skin surrounding the wound, the wound dressing comprising at least one substantially flexible substrate supporting a plurality of sensors, a first sensor of the plurality of sensors positioned on the substrate and configured to obtain a measurement of the skin surrounding the wound and at least one of the plurality of sensors and the at least one substantially flexible substrate supporting the plurality of sensors are configured to be in direct contact with the wound;
wherein the at least one substantially flexible substrate is a substantially flexible printed circuit.

22. The apparatus of claim 21, wherein a second sensor of the plurality of sensors is positioned on the at least one substantially flexible substrate and configured to obtain a measurement of the wound.

23. The apparatus of claim 21, wherein the at least one substantially flexible substrate is sized to be extend at least partially beyond the area of the wound and configured to be positioned at least partially over skin surrounding the wound.

24. The apparatus of claim 21, wherein the wound dressing comprises a wound contact layer.

25. The apparatus of claim 21, wherein the at least one substantially flexible substrate comprises a substantially flexible non-conducting mesh.

26. The apparatus of claim 21, wherein the substantially flexible printed circuit comprises a flexible polymer.

27. The apparatus of claim 25, wherein at least some of the plurality of sensors are electrically connected with each other, and wherein the plurality of sensors is configured to be electrically connected with a controller and a power source.

28. The apparatus of claim 27, wherein the controller is configured to receive data from the plurality of sensors and communicate the received data to a computing device configured to process the received data to determine one or more conditions associated with the wound.

29. The apparatus of claim 28, wherein the at least one of the controller or the computing device is configured to indicate, based on the one or more conditions associated with the wound, that the wound is healing.

30. The apparatus of claim 21, wherein the plurality of sensors comprises one or more temperature sensors, conductivity sensors, multispectral optical measurements sensors, pH sensors, pressure sensors, colorimetric sensors, optical sensors, ultraviolet (UV) sensors, or infrared (IR) sensors.

31. The apparatus of claim 21, wherein the plurality of sensors comprises a skin elasticity sensor configured to perform an ultrasound sweep of a region of the skin surrounding the wound.

32. A method of operating a wound monitoring apparatus, the method comprising:
monitoring at least one of a wound or skin surrounding the wound with a wound dressing configured to be positioned in contact with a wound, the wound dressing comprising at least one substantially flexible substrate supporting a plurality of sensors, wherein at least one of the plurality of sensors and the at least one substantially flexible substrate supporting the plurality of sensors are configured to be in direct contact with the wound; and
wherein the at least one substantially flexible substrate is a substantially flexible printed circuit.

* * * * *

UNITED STATES PATENT AND TRADEMARK OFFICE
CERTIFICATE OF CORRECTION

PATENT NO. : 11,717,447 B2
APPLICATION NO. : 16/301388
DATED : August 8, 2023
INVENTOR(S) : Varuni Rachindra Brownhill It is certified that error appears in the above-identified patent and that said Letters Patent is hereby corrected as shown below:

In the Specification

In Column 5, Line 50, delete "sterniotomies," and insert --sternotomies,--.

In Column 13, Line 22, delete "bridge" and insert --bridge.--.

In Column 19, Line 11, delete "fluropolymers" and insert --fluoropolymers--.

In Column 21, Line 49, delete "FIG." and insert --FIGS.--.

In Column 22, Line 16, delete "FIG." and insert --FIGS.--.

In Column 22, Line 43, delete "environment" and insert --environment.--.

In Column 24, Line 5, delete "lie" and insert --1/e--.

In Column 24, Lines 8-10, delete "$I(x) = I_{0e-x\mu(\lambda)}$" and insert --$I(x) = Ioe - x\mu(\lambda)$--.

In Column 24, Line 44, delete "Autoflourescense" and insert --Autofluorescence--.

In Column 31, Line 66, delete "FIG." and insert --FIGS.--.

In the Claims

In Column 34, Claim 8, Line 43, delete "wireles sly" and insert --wirelessly--.

Signed and Sealed this
Twenty-fourth Day of October, 2023

Katherine Kelly Vidal
*Director of the United States Patent and Trademark Office*